US010738121B2

(12) United States Patent
Arnaout

(10) Patent No.: US 10,738,121 B2
(45) Date of Patent: Aug. 11, 2020

(54) THERAPEUTIC USE OF INTEGRIN-BINDING ANTIBODIES

(71) Applicant: The General Hospital Corporation, Boston, MA (US)

(72) Inventor: M. Amin Arnaout, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/553,925

(22) PCT Filed: Feb. 29, 2016

(86) PCT No.: PCT/US2016/020133
§ 371 (c)(1),
(2) Date: Aug. 25, 2017

(87) PCT Pub. No.: WO2016/138538
PCT Pub. Date: Sep. 1, 2016

(65) Prior Publication Data
US 2018/0244782 A1    Aug. 30, 2018

Related U.S. Application Data

(60) Provisional application No. 62/134,394, filed on Mar. 17, 2015, provisional application No. 62/132,642, filed on Mar. 13, 2015, provisional application No. 62/126,755, filed on Mar. 2, 2015, provisional application No. 62/121,656, filed on Feb. 27, 2015.

(51) Int. Cl.
| A61K 39/395 | (2006.01) |
| A61K 39/00 | (2006.01) |
| C07K 16/28 | (2006.01) |
| A61P 13/12 | (2006.01) |

(52) U.S. Cl.
CPC .......... *C07K 16/2845* (2013.01); *A61P 13/12* (2018.01); *A61K 2039/505* (2013.01); *C07K 2317/24* (2013.01); *C07K 2317/56* (2013.01); *C07K 2317/565* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| 7,998,738 B2* | 8/2011 | Arnaout ............ C07K 16/2845 435/326 |
| 2005/0069541 A1 | 3/2005 | Karlik |
| 2005/0227296 A1 | 10/2005 | Arnaout |
| 2005/0260193 A1 | 11/2005 | Lieberburg |
| 2006/0110394 A1 | 5/2006 | Bendig et al. |
| 2010/0047252 A1 | 2/2010 | Mach |
| 2011/0039722 A1 | 2/2011 | Takeuchi et al. |
| 2012/0010255 A1 | 1/2012 | Gupta |

FOREIGN PATENT DOCUMENTS

| WO | 1993/021953 | 11/1993 |
| WO | 2013/159082 | 10/2013 |

OTHER PUBLICATIONS

Chopp et al. Postischemic Administration of an Anti-Mac-1 Antibody Reduces Ischemic Cell Damage After Transient Middle Cerebral Artery Occlusion in RatsStroke 1994, 25:869-876. (Year: 1994).*
Zhang et al. Postischemic treatment (2-4 h) with anti-CDIIb and anti-CD18 monoclonal antibodies are neuroprotective after transient (2 h) focal cerebral ischemia in the rat. Brain Research 698(1995) 79-85. (Year: 1995).*
Jiang et al. Anti-CDIIb Monoclonal Antibody Reduces Ischemic Cell Damage After Transient (2h) but Not After Permanent MCA Occlusion in the Rat (Neuroscience Research Communications, 15(2), p. 85-93, 1994). (Year: 1994).*
Chen et al. Anti-CD11b monoclonal antibody reduces ischemic cell damage after transient focal cerebral ischemia in rat. Ann Neurol. Apr. 1994;35(4):458-63. (Year: 1994).*
Jaeschke et al. Functional inactivation of neutrophils with a Mac-1 (CD11b/CD18) monoclonal antibody protects against ischemia-reperfusion injury in rat liver. Hepatology. May 1993;17(5):915-23. (Year: 1993).*
Annenkov et al., "The beta 2 integrin Mac-1 but not p150,95 associates with Fc gamma RIIA," Eur J Immunol, 1996, 26: 207-212.
Arnaout, "Structure and function of the leukocyte adhesion molecules CD11/CD18," Blood, 1990, 75: 1037-1050.
Aster et al., "Drug-induced immune thrombocytopenia: pathogenesis, diagnosis, and management," J Thromb Haemost, 2009, 7: 911-918.
Booster et al., "Inhibition of CD18-dependent leukocyte adherence by mAb 6.5 E does not prevent ischemia-reperfusion injury as seen in grafted kidneys," Transpl Int, 1995, 8: 126-132.
Boros and Bromberg, "New cellular and molecular immune pathways in ischemia/reperfusion injury," Am J Transplant, 2006, 6: 652-658.
Castano et al., "Serum amyloid P inhibits fibrosis through Fc gamma R-dependent monocyte-macrophage regulation in vivo," Sci Transl Med, Nov. 2009, 1: 5ra13.
Chertow et al., "Acute kidney injury, mortality, length of stay, and costs in hospitalized patients," Journal of the American Society of Nephrology, 2005, 16: 3365-3370.
Cox et al., "Integrins as therapeutic targets: lessons and opportunities," Nat Rev Drug Discov, 2010, 9: 804-820.
Devarajan, "Update on mechanisms of ischemic acute kidney injury," Journal of the American Society of Nephrology, 2006, 17: 1503-1520.

(Continued)

*Primary Examiner* — Maher M Haddad
(74) *Attorney, Agent, or Firm* — Fish & Richardson P.C.

(57) ABSTRACT

This disclosure relates to therapeutic use of integrin-binding antibodies.

4 Claims, 9 Drawing Sheets

Specification includes a Sequence Listing.

(56) References Cited

OTHER PUBLICATIONS

Eltzschig and Eckle, "Ischemia and reperfusion—from mechanism to translation," Nature Medicine, 2011, 17: 1391-1401.

Evangelista et al., "Platelet/polymorphonuclear leukocyte interaction in dynamic conditions: evidence of adhesion cascade and cross talk between P-selectin and the beta 2 integrin CD11b/CD18," Blood, 1996, 88: 4183-4194.

Flores et al., "The role of cell swelling in ischemic renal damage and the protective effect of hypertonic solute," The Journal of Clinical Investigation , 1972, 51: 118-126.

Haug et al., "Real-time monitoring of renal function during ischemic injury in the rhesus monkey," Ren Fail, 1995, 17: 489-502.

Hsu, "Yes, AKI truly leads to CKD," Journal of the American Society of Nephrology, 2012, 23: 967-969.

Ingalls et al., "Outside-in signaling by lipopolysaccharide through a tailless integrin," J Immunol, Jul. 1997, 159: 433-438.

International Preliminary Report on Patentability in International Application No. PCT/US2016/020133, dated Aug. 29, 2017, 16 pages.

Jakus et al., "Responses of neutrophils to anti-integrin antibodies depends on costimulation through low affinity Fc gamma Rs: full activation requires both integrin and nonintegrin signals," J Immunol, 2004,173: 2068-2077.

Kamata et al., "The role of the CPNKEKEC sequence in the beta(2) subunit I domain in regulation of integrin alpha(L)beta(2) (LFA-1)," J Immunol, 2002, 168: 2296-2301.

Kielar et al., "Maladaptive role of IL-6 in ischemic acute renal failure," Journal of the American Society of Nephrology, 2005, 16: 3315-3325.

Li et al., "Characterization of a conformationally sensitive murine monoclonal antibody directed to the metal ion-dependent adhesion site face of integrin CD11b," J Immunol, 2002, 168: 1219-1225.

Li et al., "NKT cell activation mediates neutrophil IFN-gamma production and renal ischemia-reperfusion injury," J Immunol, 2007, 178: 5899-5911.

Ling et al., "Integrin CD11b positively regulates TLR4-induced signalling pathways in dendritic cells but not in macrophages," Nat Commun, 2014, 5: 3039.

Lo et al., "Dialysis-requiring acute renal failure increases the risk of progressive chronic kidney disease," Kidney International, 2009, 76: 893-899.

Mahalingam et al., "Stable coordination of the inhibitory Ca2+ ion at the metal ion-dependent adhesion site in integrin CD11b/CD18 by an antibody-derived ligand aspartate: implications for integrin regulation and structure-based drug design," J Immunol, 2011, 187: 6393-6401.

Moers et al., "Machine perfusion or cold storage in deceased-donor kidney transplantation," N Engl J Med, 2009, 360: 7-19.

Parkos et al., "Neutrophil migration across a cultured intestinal epithelium. Dependence on a CD11b/CD18-mediated event and enhanced efficiency in physiological direction," The Journal of Clinical Investigation, 1991, 88: 1605-1612.

Rabb et al., "Role of CD11a and CD11b in ischemic acute renal failure in rats," Am J Physiol, Dec. 1994, 267: F1052-1058.

Rezzonico et al., "Ligation of CD11b and CD11c beta(2) integrins by antibodies or soluble CD23 induces macrophage inflammatory protein 1alpha (MIP-1alpha) and MIP-1beta production in primary human monocytes through a pathway dependent on nuclear factor-kappaB," Blood, 2001, 97: 2932-2940.

Rifkin et al., "Does AKI truly lead to CKD?," Journal of the American Society of Nephrology, 2012, 23: 979-984.

Siedlecki et al., "Delayed graft function in the kidney transplant," Am J Transplant, 2011, 11: 2279-2296.

Summers and Jamison, "The no reflow phenomenon in renal ischemia," Lab Invest, 1971, 25: 635-643.

Tajra et al., "In vivo effects of monoclonal antibodies against rat beta(2) integrins on kidney ischemia-reperfusion injury," J Surg Res, Nov. 1999, 87: 32-38.

Thornton et al., "An evaluation of the neutrophil as a mediator of in vivo renal ischemic-reperfusion injury," The American Journal of Pathology, 1989, 135: 509-515.

Van Spriel et al., "Mac-1 (CD11b/CD18) is essential for Fc receptor-mediated neutrophil cytotoxicity and immunologic synapse formation," Blood, 2001, 97: 2478-2486.

Wagner et al., "The complement receptor 3, CR3 (CD11b/CD18), on T lymphocytes: activation-dependent up-regulation and regulatory function," Eur J Immunol, 2001, 31: 1173-1180.

Wang et al., "Partial depletion of macrophages by ED7 reduces renal injury in Adriamycin nephropathy," Nephrology, 2005, 10: 470-477.

Wu et al., "TLR4 activation mediates kidney ischemia/reperfusion injury," The Journal of Clinical Investigation, 2007, 117: 2847-2859.

Zhou and Brown, "CR3 (Mac-1, alpha M beta 2, CD11b/CD18) and Fc gamma RIII cooperate in generation of a neutrophil respiratory burst: requirement for Fc gamma RIII and tyrosine phosphorylation," The Journal of Cell Biology, 1994, 125: 1407-1416.

Johnson et al., Up-regulation of the granulocyte adhesion molecule Mac-1 by autoantibodies in autoimmune vasculitis. Clin Exp 1 mmunol. Mar. 1997, vol. 107, No. 3, pp. 5137519.

Galkina et al., Leukocyte recruitment and vascular injury in diabetic nephropathy. J Am Soc Nephrol. Feb. 2006, vol. 17, No. 2, pp. 368-377.

International Search and Written Opinion dated Aug. 23, 2016, 29 pages.

* cited by examiner

Mouse mAb107 heavy chain (H-chain)

[QVQLQQSGAELVKPGASVKLSCTPSGFNIKDIYMQWVKQRPEQGLEWIGRIDPANDKTKYDPKFQGKATITADTSSNTA
YLQLSSLTSEDTAVYYCASEGHYGYDGYAMDYWGQGTTVTVSS]AKTTPPSVYPLAPGSAAQTNSMVTLGCLVKGYFPEP
VTVTWNSGSLSSGVHTFPAVLQSDLYTLSSSVTVPSSPRPSETVTCNVAHPASSTKVDKKIVPRDC

CDR1, 2 and 3 of each is underlined. Text in brackets represents the VH region.

FIG. 7

Mouse mAb107 light chain (L-chain)
[DIEMTQSPSSLGVSVGEKVTMSCKSSQNLLYSSNQKNYLAWYQQKPGQSPKLLIYWASTRESGVPDRFTGTGSGTDFTL
TISSVKAEDLAVYYCQQYYSYPLTFGAGTKLELK]RADAAPTVSIFPPSSEQLTSGGASVVCFLNNFYPKDINVKWKIDG
SERQNGVLNSWTDQDSKDSTYSMSSTLTLTKDEYERHNSYTCEATHKTSTSPIVKSFNRNEC CDR1, 2 and 3 of each is underlined. Text in brackets represents the VL region.

FIG. 8

Humanized mAb107 VH

Humanized mAb107 VL

A humanized single chain variable fragment of 107 (scVF) with a linker linking VH and VL segments

|   |   |   |   |   |   |   |   |   |   |   |   |   |   |   |   |   |   |   |   |   |
|---|---|---|---|---|---|---|---|---|---|---|---|---|---|---|---|---|---|---|---|---|
|   |   | M | V | Q | L | V | E | S | G | G | G | L | V | Q | P | G | G | S | L |   |
| R | L | S | C | A | A | S | G | F | N | I | K | D | T | Y | I | H | W | V | R |   |
| Q | A | P | G | K | G | L | E | W | V | A | R | I | D | P | A | N | D | K | T |   |
| R | Y | A | D | S | V | K | G | R | F | T | I | S | A | D | T | S | K | N | T |   |
| A | Y | L | Q | M | N | S | L | R | A | E | D | T | A | V | Y | Y | C | S | S |   |
| E | G | H | Y | G | Y | D | G | Y | A | M | D | Y | W | G | Q | G | T | L | V |   |
| T | V | S | S | [G | G | G | G | S | G | G | G | G | S | G | G | G | G | S] | D |   |
| I | V | M | S | Q | S | P | D | S | L | A | V | S | L | G | E | R | V | T | L |   |
| N | C | K | S | S | Q | N | L | L | Y | S | S | N | Q | K | N | Y | L | A | W |   |
| Y | Q | Q | K | P | G | Q | S | P | K | L | L | I | Y | W | A | S | A | R | E |   |
| S | G | V | P | D | R | F | S | G | S | G | S | G | T | D | F | T | L | T | I |   |
| S | S | V | Q | A | E | D | V | A | V | Y | Y | C | Q | Q | Y | Y | S | Y | P |   |
| L | T | F | G | A | G | T | K | L | E | L | K |   |   |   |   |   |   |   |   |   |

CDRs are underlined. The linker that links VH and VL segments is indicated by brackets.

FIG. 11

THERAPEUTIC USE OF INTEGRIN-BINDING ANTIBODIES

CLAIM OF PRIORITY

This application is a 371 national stage application of PCT/US2016/020133, filed on Feb. 29, 2016, and which, in turn, claims the benefit of U.S. Provisional Application Ser. No. 62/134,394, filed on Mar. 17, 2015; U.S. Provisional Application Ser. No. 62/132,642, filed on Mar. 13, 2015; U.S. Provisional Application Ser. No. 62/126,755, filed on Mar. 2, 2015; and U.S. Provisional Application Ser. No. 62/121,656, filed on Feb. 27, 2015. The entire contents of the foregoing are incorporated herein by reference.

FEDERALLY SPONSORED RESEARCH OR DEVELOPMENT

This invention was made with government support under grants Nos. DK088327, DK48549 and DK007540 awarded by the National Institutes of Health. The government has certain rights in the invention.

TECHNICAL FIELD

This disclosure relates to therapeutic use of integrin-binding antibodies.

BACKGROUND

Integrins are heterodimeric receptors that mediate interactions both between cells and between cells and the extracellular matrix via ligand binding. Many integrins are thought to exist in two conformations, a low affinity state (the "closed" or "unliganded" conformation") and a high affinity state (the "open" or "liganded" conformation), the latter of which is responsible for high affinity ligand binding. Antibody to integrins have been developed. A ligand-mimetic monoclonal antibody mAb 107, produced by a hybridoma cell line, that can bind to CD11b in an activation-independent manner has been described, e.g., in U.S. Pat. No. 7,998,738.

As integrins transduce signals that mediate the effects of the matrix on the physiological activity of cells, there is considerable interest in developing therapeutic use of integrin-binding antibodies.

SUMMARY

This disclosure relates to therapeutic use of integrin-binding antibodies.

In one aspect, the disclosure relates to a method of ameliorating a pathology associated with ischemia reperfusion injury in a subject. The method includes administering to the subject a therapeutically effective amount of composition having a polypeptide that immunospecifically binds the epitope recognized by mab107.

In some embodiments, the pathology is post-ischemic renal fibrosis, a kidney fibroinflammatory disease, pulmonary fibrosis, or post-myocardial infarction left ventricular adverse remodeling.

The disclosure also relates to a method of treating a subject having a disorder associated with ischemia reperfusion injury in an organ. The method includes administering to the subject a therapeutically effective amount of composition having a polypeptide that immunospecifically binds the epitope recognized by mab107.

In some embodiments, the organ is a kidney, a heart, or a lung. In some embodiments, the disorder is acute kidney injury, acute coronary syndrome, acute myocardial infarction (MI).

In some embodiments, the therapeutically effective amount of composition having a polypeptide that immunospecifically binds the epitope recognized by mab107 is administered to the subject within about 5 hours after the ischemia reperfusion injury, within about 4 hours after the ischemia reperfusion injury, within about 3 hours after the ischemia reperfusion injury, within about 2 hours after the ischemia reperfusion injury, within about 1.5 hours after the ischemia reperfusion injury, or within about 1 hour after the ischemia reperfusion injury.

The disclosure also relates to a method of providing an organ for transplantation. The method includes administering to an organ donor a composition having a polypeptide that immunospecifically binds the epitope recognized by mab107; and harvesting the organ from the organ donor.

The disclosure also relates to a method of reducing delayed graft function following organ transplantation. The method includes administering to an organ recipient a therapeutically effective amount of composition having a polypeptide that immunospecifically binds the epitope recognized by mab107 prior to transplantation of the organ to the recipient or within a day of the transplantation, thereby reducing delayed graft function following organ transplantation.

The disclosure also relates to a method of treating an organ prior to transplantation into a recipient. The method includes contacting the organ with a composition having a polypeptide that immunospecifically binds the epitope recognized by mab107.

In some embodiments, the transplanted organ is a kidney, a heart, or a lung.

In some embodiments, the organ contacts the composition having a polypeptide that immunospecifically binds the epitope recognized by mab107 through perfusion fluid.

The disclosure also relates to a method of treating a subject having an autoimmune disease. The method includes administering to the subject a therapeutically effective amount of composition having a polypeptide that immunospecifically binds the epitope recognized by mab107. In some embodiments, the autoimmune disease is cytoplasmic antineutrophil cytoplasmic antibodies (cANCA)-associated vasculitis.

The disclosure also relates to a method of treating a subject having diabetic nephropathy. The method includes administering to the subject a therapeutically effective amount of composition having a polypeptide that immunospecifically binds the epitope recognized by mab107.

The disclosure also relates to a method of ameliorating a pathology associated with chemotherapy in a subject. The method includes administering to the subject a therapeutically effective amount of composition having a polypeptide that immunospecifically binds the epitope recognized by mab107. In some embodiments, the pathology is Adriamycin nephropathy.

In some embodiments, the polypeptide that immunospecifically binds the epitope recognized by mab107 is mab107.

In some embodiments, the polypeptide that immunospecifically binds the epitope recognized by mab107 is humanized.

In some embodiments, the polypeptide that immunospecifically binds the epitope recognized by mab107 is a single chain variable fragments (scFv).

In some embodiments, the polypeptide that immunospecifically binds the epitope recognized by mab107 comprises one, two, three, four, five, or six of the following complementarity determining regions (CDR):

1) CDR 1 of the VH of mab107;
2) CDR 1 of the VL of mab107;
3) CDR 2 of the VH of mab107;
4) CDR 2 of the VL of mab107;
5) CDR3 of the VH of mab107; and
6) CDR 3 of the VL of mab107.

In all of the embodiments described here the polypeptide that immunospecifically binds the epitope recognized by mab107 can be an antibody.

In various embodiments the polypeptide or antibody that immunospecifically binds the epitope recognized by mab107 comprises an amino acid sequence that comprises an amino acid sequence at least 95%, 98%, or 100% identical to an amino acid sequence selected from the group consisting of:

(SEQ ID NO: 1)
QVQLQQSGAELVKPGASVKLSCTPSGFNIKDIYMQWVKQRPEQGLEW

IGRIDPANDKTKYDPKFQGKATITADTSSNTAYLQLSSLTSEDTAVY

YCASEGHYGYDGYAMDYWGQGTTVTVSS;

(SEQ ID NO: 2)
DIEMTQSPSSLGVSVGEKVTMSCKSSQNLLYSSNQKNYLAWYQQKPG

QSPKLLIYWASTRESGVPDRFTGTGSGTDFTLTISSVKAEDLAVYYC

QQYYSYPLTFGAGTKLELK;

(SEQ ID NO: 3)
VQLVESGGGLVQPGGSLRLSCAASGFNIKDTYIHWVRQAPGKGLEWV

ARIDPANDKTRYADSVKGRFTISADTSKNTAYLQMNSLRAEDTAVYY

CSSEGHYGYDGYAMDYWGQGTLVTVSS;

(SEQ ID NO: 4)
DIVMSQSPDSLAVSLGERVTLNCKSSQNLLYSSNQKNYLAWYQQKPG

QSPKLLIYWASARESGVPDRFSGSGSGTDFTLTISSVQAEDVAVYYC

QQYYSYPLTFGAGTKLELK;
and (SEQ ID NO: 5)
MVQLVESGGGLVQPGGSLRLSCAASGFNIKDTYIHWVRQAPGKGLEW

VARIDPANDKTRYADSVKGRFTISADTSKNTAYLQMNSLRAEDTAVY

YCSSEGHYGYDGYAMDYWGQGTLVTVSSGGGGSGGGGSGGGGSDIVM

SQSPDSLAVSLGERVTLNCKSSQNLLYSSNQKNYLAWYQQKPGQSPK

LLIYWASARESGVPDRFSGSGSGTDFTLTISSVQAEDVAVYYCQQYY

SYPLTFGAGTKLELK.

In some embodiments the polypeptide or antibody that immunospecifically binds the epitope recognized by mab107 comprises an amino acid sequence that comprises an amino acid sequence at least 95% or 98% identical to an amino acid sequence selected from the group consisting of:

(SEQ ID NO: 1)
QVQLQQSGAELVKPGASVKLSCTPSGFNIKDIYMQWVKQRPEQGLEW

IGRIDPANDKTKYDPKFQGKATITADTSSNTAYLQLSSLTSEDTAVY

YCASEGHYGYDGYAMDYWGQGTTVTVSS;

(SEQ ID NO: 2)
DIEMTQSPSSLGVSVGEKVTMSCKSSQNLLYSSNQKNYLAWYQQKPG

QSPKLLIYWASTRESGVPDRFTGTGSGTDFTLTISSVKAEDLAVYYC

QQYYSYPLTFGAGTKLELK;

(SEQ ID NO: 3)
VQLVESGGGLVQPGGSLRLSCAASGFNIKDTYIHWVRQAPGKGLEWV

ARIDPANDKTRYADSVKGRFTISADTSKNTAYLQMNSLRAEDTAVYY

CSSEGHYGYDGYAMDYWGQGTLVTVSS;

(SEQ ID NO: 4)
DIVMSQSPDSLAVSLGERVTLNCKSSQNLLYSSNQKNYLAWYQQKPG

QSPKLLIYWASARESGVPDRFSGSGSGTDFTLTISSVQAEDVAVYYC

QQYYSYPLTFGAGTKLELK;
and (SEQ ID NO: 5)
MVQLVESGGGLVQPGGSLRLSCAASGFNIKDTYIHWVRQAPGKGLEW

VARIDPANDKTRYADSVKGRFTISADTSKNTAYLQMNSLRAEDTAVY

YCSSEGHYGYDGYAMDYWGQGTLVTVSSGGGGSGGGGSGGGGSDIVM

SQSPDSLAVSLGERVTLNCKSSQNLLYSSNQKNYLAWYQQKPGQSPK

LLIYWASARESGVPDRFSGSGSGTDFTLTISSVQAEDVAVYYCQQYY

SYPLTFGAGTKLELK, provided that the under lined portions of the sequence are not altered.

The term "epitope" as used herein refers to a protein determinant capable of binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

As used herein, the term "ischemia reperfusion injury" refers to an injury of organs caused by putting the organs into an ischemic condition and/or an injury of organ occurred after reperfusion.

As used herein, the term "treatment" or "treating a subject" refers to the application or administration of a therapeutic agent to a patient, or application or administration of a therapeutic agent to an isolated tissue or cell line from a subject, who has a disease, a symptom of disease or a predisposition toward a disease, with the purpose to cure, heal, alleviate, relieve, alter, remedy, ameliorate, palliate, improve or affect the disease, the symptoms of disease or the predisposition toward disease.

The term "purified" as used herein, refers to other molecules, e.g. polypeptide, nucleic acid molecule that have been identified and separated and/or recovered from a component of its natural environment. Thus, in some embodiments, the polypeptides are purified polypeptides wherein they have been separated from one or more components of their natural environment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 2a. Serum levels of mAbs 107 and X63 in treated (A1) and control (C1) monkeys 24 hours after I/R. FIG. 2b. Serum creatinine (sCR) prior to (day 0, d0) and one day (d1) after ischemia-reperfusion (FR). sCR returned to normal after clamp release (arrow). FIG. 2c. Time of no-reflow in A1 and C1. FIG. 2d. White blood cell (WBCs) levels measured prior to (d0) and 1 (d1), 2(d2) and 5(d5) days after I/R. FIG. 2e. Neutrophil levels measured prior to (d0) and 1 (d1), 2(d2) and 5(d5) days after I/R. FIG. 2f. Monocyte levels measured prior to (d0) and 1 (d1), 2(d2) and 5(d5) days after I/R. FIG. 2g. Lymphocyte levels measured prior to (d0) and 1 (d1), 2(d2) and 5(d5) days after I/R. FIG. 2h. Platelet levels measured prior to (d0) and 1 (d1), 2(d2) and 5(d5) days after I/R. FIG. 2i. Hematocrit (HCT) levels measured prior to (d0) and 1 (d1), 2(d2) and 5(d5) days after I/R. FIG. 2j. Histograms showing binding of mAb 24 to FMLF-activated PMNs from two different naïve monkeys in the absence of presence of the Fab fragment of mAb107. MFI, mean fluorescence units. FIG. 2k. Histograms showing binding of mAb 24 to PMNs from A1 and C1 monkeys. PMNs were isolated 1 day after FR. FIG. 2l. Flow cytometric analysis of the PMNs studies in n, unstained and following staining with FITC-labeled anti-mouse Ig. FIG. 2m. Blood urea nitrogen (BUN) levels 2 days (–d2) and one day (–d1) prior to planned euthanasia (d0). Left ureter was ligated on –d2 (arrows) after blood was withdrawn. FIG. 2n. sCR levels 2 days (–d2) and one day (–d1) prior to planned euthanasia (d0). Left ureter was ligated on –d2 (arrows) after blood was withdrawn. FIG. 2o. Gross appearance of harvested left and right kidneys from C1 and A1. FIG. 2p. Histograms showing average number of macrophages in 20 high power (200×) fields. FIG. 2q. Histograms showing the fibrosis area (trichrome stain-positive) presented as % of total area in ten fields at 20× magnification.

FIG. 3a. Serum levels of mAbs 107 treated monkeys A2-A4 and A5) 24 hours after I/R. FIG. 3b. Histograms (mean±SD) showing time of no-reflow in mAb107-treated and controls. Data are shown as mean'SD. FIG. 3c. White blood cell (WBCs) levels in treated (A) and controls (C) measured prior on d0, d1, d2 and d5 after I/R. Data are shown as mean+SD. FIG. 3d. Neutrophil levels in treated (A) and controls (C) measured prior on d0, d1, d2 and d5 after FR. Data are shown as mean+SD. FIG. 3e. Monocyte levels in treated (A) and controls (C) measured prior on d0, d1, d2 and d5 after I/R. Data are shown as mean+SD. FIG. 3f. Lymphocyte levels in treated (A) and controls (C) measured prior on d0, d1, d2 and d5 after FR. Data are shown as mean+SD. FIG. 3g. Platelet levels in treated (A) and controls (C) measured prior on d0, d1, d2 and d5 after I/R. Data are shown as mean+SD. FIG. 3h. Hematocrit (HCT) levels in treated (A) and controls (C) measured prior on do, d1, d2 and d5 after I/R. Data are shown as mean+SD. FIG. 3i. BUN levels on d0 prior to ischemia, on d1, d2 after ligation of left ureter and on d5 after clamp release. Data are shown as mean+SD. FIG. 3j. sCR levels on d0 prior to ischemia, on d1, d2 after ligation of left ureter and on d5 after clamp release. Data are shown as mean+SD.

FIG. 4a. BUN levels 2 days (–d2) and one day (–d1) prior to planned euthanasia (d0). Left ureter was ligated on d2(arrows) after blood was withdrawn. FIG. 4b. sCR levels 2 days (–d2) and one day (–d1) prior to planned euthanasia (d0). Left ureter was ligated on –d2 (arrows) after blood was withdrawn. FIG. 4c. Representative, gross appearance of left and right kidneys from control (C4) monkeys harvested 9 months after AKI. FIG. 4d. Representative, gross appearance of left and right kidneys from treated (A4) monkeys harvested 9 months after AKI. FIG. 4e. Histograms (mean±SD) showing average number of macrophages deposition. FIG. 4f. Histograms (mean±SD) showing average number of collagen deposition. FIG. 4g. Histograms (mean±SD) showing degree of fibrosis. FIG. 4h. Representative sections of control right kidney harvested 9 months after AKI. FIG. 4i. Representative sections of treated right kidney harvested 9 months after AKI.

FIG. 5a. Cytokine/chemokine and complement C3 levels in right kidney biopsies 1-2 days after AKI, 3 (A1) and 9 (A2) months later in two treated (A1, A2) and control animals. FIG. 5b. Cytokine/chemokine and complement C3 levels in left and right kidneys 3 (A1) months after AKI in treated and control animals.

FIG. 7. Amino acid sequences of mouse mAb107 heavy chain (H-chain). Complementarity determining regions (CDR) are underlined. Text in brackets represents the VH region.

FIG. 8. Amino acid sequences of mouse mAb107 light chain (L-chain). CDRs are underlined. Text in brackets represents the VL region.

FIG. 9. Amino acid sequences of humanized mAb107 VH. CDRs are underlined.

FIG. 10. Amino acid sequences of humanized mAb107 VH. CDRs are underlined.

FIG. 11. Amino acid sequences of a humanized single chain variable fragment of 107 (scFv) with a linker (in brackets) linking VH and VL segments. CDRs are underlined.

DETAILED DESCRIPTION

Figure 1:
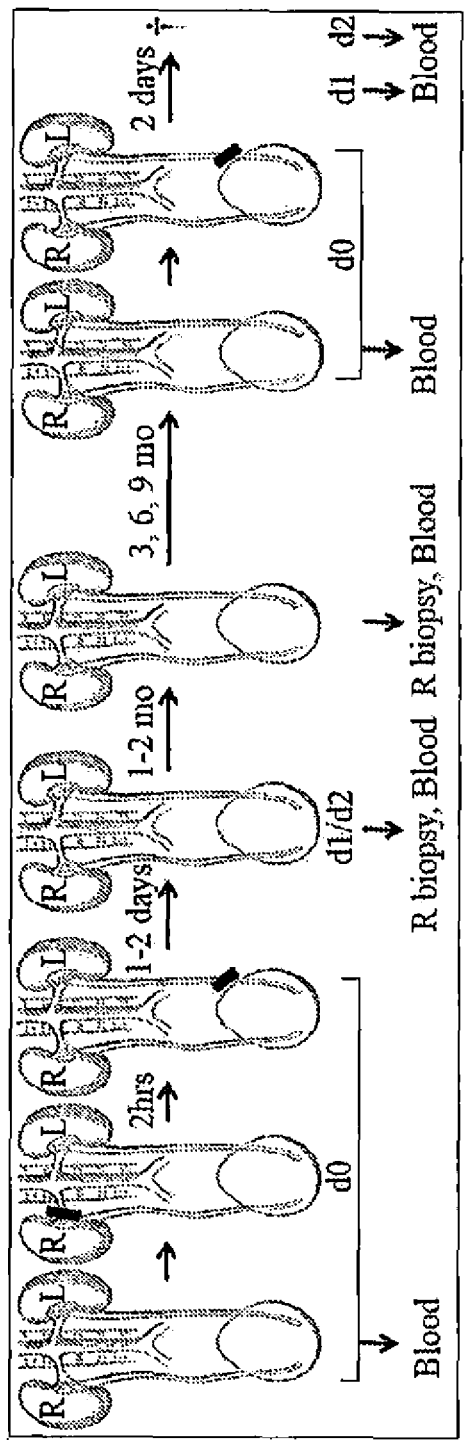
FIG. 1. Schematic of the protocol used to develop a chronic kidney disease (CKD) model.

The present disclosure is based, in part, on the observation that a polypeptide that immunospecifically binds the epitope recognized by mab107 has various therapeutic uses, e.g., in treating disorders associated with ischemia reperfusion injury.

Ischemia reperfusion injury are injuries caused by putting the organs into an ischemic condition and/or an injury of organ occurred after reperfusion. Ischemia generally refers to a restriction in blood supply to tissues, causing a shortage of oxygen and glucose needed for cellular metabolism. Reperfusion injury is the tissue damage caused when blood supply returns to the tissue after a period of ischemia. The absence of oxygen and nutrients from blood during the ischemic period creates a condition in which the restoration of circulation results in inflammation and oxidative damage through the induction of oxidative stress rather than restoration of normal function.

Acute kidney injury (AKI), an inflammatory disease often caused by ischemia-reperfusion (I/R)[1,2], is a common and growing burden for the healthcare system worldwide[3,4]. AKI appears to incur long-term risks of developing chronic fibrosis and end stage renal disease (ESRD) in humans, especially following severe (dialysis-requiring) injury to native or transplanted kidneys[5-7].

Ischemic acute kidney injury is a strong predictor of progression to fibrotic chronic kidney disease (CKD). The lack of effective therapies is due in part to the scarcity of animal models of CKD, especially in nonhuman primates. The innate immune system plays an important role in ischemic AKI but its contribution to progression to fibrotic kidney disease is less clear.

This disclosure provides a model of post-ischemic CKD in Cynomolgus monkeys and assesses the potential role of the archetypal innate immune receptor CD11b/CD18 (Complement Receptor 3) in progression to CKD.

The studies below describe the use of mAb107 (deposited in the American Type Culture Collection under Accession Number ATCC PTA-11614), a murine antibody that behaves as a ligand mimic. Earlier studies have shown that mAb107 binds in a divalent-cation-dependent manner to solvent-exposed residues on the MIDAS face of CD11b, blocks interaction of 11bA or the holoreceptor with ligands, and inhibits spreading and phagocytosis by human neutrophils. However, in contrast to physiologic ligands, mAb 107 preferentially binds to the inactive low-affinity form of the integrin, suggesting that its antagonistic effects are exerted in part by stabilizing the receptor in the low-affinity state.

A 2-hour unilateral right kidney vascular occlusion followed by reperfusion was induced in 10 animals, with subsequent periods of left ureter ligation to assess right kidney function. Early inactivation of CD11b/CD18 in five animals using mAb107 improved microvascular perfusion and reduced key pro-inflammatory mediators in the right kidney, but did not significantly improve right kidney function 1-2 days post AKI. However, mAb107 salvaged kidney function from otherwise irreversible fibrotic right kidney failure in all treated animals three, six and nine months after ischemic AKI. These studies reveal an unsuspected critical early role of CD11b+ innate immune cells in post-ischemic chronic fibrosis in non-human primates, and a potential therapeutic approach to prevent progression to CKD in the clinical setting.

Prolonged renal hypoperfusion is the most frequent cause of intrinsic AKI in hospitalized patients[5]. Controversy currently exists as to whether AKI per se causes CKD and ESRD[39,40], given that patients who develop AKI tend to be older with a higher burden of comorbidities that could serve as more direct causes. The CKD model clearly shows that severe I/R AKI is the direct cause of ESRD in previously healthy cynomolgus monkeys. Using this model, we also show that early inactivation of the innate immune receptor CD11b/CD18 (CR3) interrupts the irreversible course of progressive kidney failure caused by severe I/R AKI. Five of five control animals subjected to severe I/R in this study lost kidney function 3, 6 and 9 months later, in contrast to all mAb107-treated animals, where life-sustaining kidney function was observed at the end of the observation periods. Histopathologic examination of interval right kidney biopsies showed progressive recovery from acute tubular necrosis induced by I/R AKI. At sacrifice, 3-9 months after the initial injury, significant reductions in intrarenal macrophages, interstitial fibrosis and collagen deposition were observed in the harvested right kidney from all treated animals vs. controls.

Ischemic injury targets renal tubular epithelial cells, peritubular capillary endothelium and the renal mononuclear phagocytic system. The resulting lethal or sublethal cell damage triggers an intrinsic inflammatory response that involves the activation of pattern recognition receptors (PRRs) by secretion of a multitude of damage-associated molecular patterns (DAMPs), and activation of the complement and coagulation systems. The proinflammatory chemokines and cytokines produced recruit circulating inflammatory cells to the kidney following reperfusion[10]. Attenuated vascular relaxation, capillary leak, complement activation, adhesion of trapped leukocytes to endothelium, platelet-leukocyte aggregation and leukoaggregation clogs capillaries[41]. Microvacular occlusion is further aggravated by the new supply of activated leukocytes and platelets after resumption of blood flow—the no-reflow phenomenon[42,43].

mAb107 did not protect renal tubular epithelial from the initiating ischemic insult, as judged functionally by the life-threatening rise in serum creatinine, and pathologically by widespread acute tubular necrosis detected in the right injured kidney one to two days after severe I/R, but mAb107 therapy salvaged kidney structure and function from otherwise irreversible fibrosis, microvascular rarefaction and organ failure 3-9 months later. One consistent and immediate response to mAb107 was a significant reduction in the no-reflow phenomenon. Prolonged microvascular no-reflow is known to increase the risk of primary kidney allograft dysfunction[44]. The observed reduction in non-reflow by CD11b/CD18 inactivation is likely related at least in part to inhibition of leukocyte adhesion-dependent damage to peritubular capillary endothelium, and prevention of intracapillary PMN-platelet and PMN-PMN aggregates.

A second early response to mAb107 therapy was a dramatic reduction in the pro-inflammatory mediators RANTES, IL18, complement C3, IL6 and IFNγ in the right kidney 1-2 days after FR, which remained low in the same kidneys when harvested several months later. These mediators are produced by ischemic parenchymal cells, as well as infiltrating leukocytes including NKT and neutrophils[12,45]. Mouse knockouts of RANTES[46], IL18[47], complement[48], IL6[45] or NKT (IFNγ) depletion partially protected kidney function 1-7 days post-ischemic AKI. Simultaneous reductions in all five proinflammatory mediators by mAb107 indicate that intrinsic and/or infiltrating CD11b+ leukocytes play a primary role in their production. The underlying mechanism is most likely secondary to inhibition of the established roles of CD11b in phagocytosis, Fcγ IIa/III[29-31] and TLR4 signaling[49], pathogenic processes associated with production of inflammatory mediators including cytokines, chemokines, complement and reactive oxygen species[33,34].

Levels of the other chemokines/cytokines measured (IL1β, TNF-α, IL8 and MCP1) in treated kidneys 1-2 days after I/R were variable, but did not correlate with long-term right kidney functional improvement in our model. This is consistent with the variable outcomes seen in rodent models of AKI, where double knockout of IL-1R and TNFR1 did not protect against ischemic AKI in mice[50] or was protective (IL8 and MCP1) in short term studies[51,52].

Interestingly, IL2, produced by activated CD4+ T cells and DCs[53] and was increased in treated right kidneys1-2 days after injury, but returned to near baseline levels in harvested right kidneys. IL-2 plays an important role in expansion and/or function of CD4+CD25+ regulatory T cells (Treg)[54], which are known to attenuate I/R AKI in rodents[14,55] Harvested mAb107-treated kidneys expressed increased levels of active TGFβ1, which is secreted by most immune cells, is required for Treg suppressor activity[56]. The early rise of IL-2, and late increase in TGFβ1 reflects the subtle shifts in cytokine and chemokine production occurring in the mAb107-treated monkeys that contribute to the late recovery of kidney function.

Figure 6:
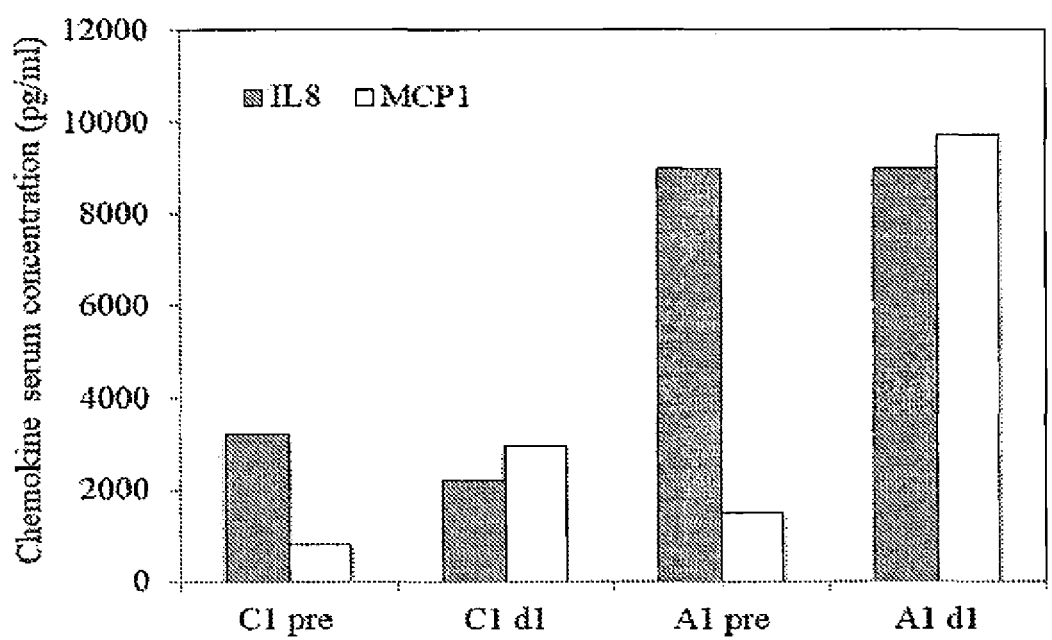
FIG. 6. Histograms showing serum levels of IL8 and MCP1 in control (C1) and treated (A1) animals prior to (pre) and 1 day after FR.

A third early and potentially relevant observation also made one day after I/R was the stabilization of CD11b/CD18 in the inactive conformation by mAb107, despite presence of high serum concentration of a variety of agonists known to switch this integrin into the active state such as IL-8 and MCP-1 (FIG. 6). The present data suggest that early targeting of CD11b/CD18 signaling with a "pure" antagonist (i.e. that dose not inadvertently activate the integrin) may provide a new approach in preventing progressive fibrosis and promoting functional recovery after ischemic AKI.

The present disclosure provides therapeutic uses of integrin-binding antibodies. In some embodiments, the described method is designed to inhibit both the initial inflammatory reaction elicited by ischemic activation of intrinsic CD11b+ immune cells, and the one following reperfusion, by giving the half the dose mAb prior to ischemia and the other half before reperfusion. In some embodiments, renal recovery can be improved further by adding a second dose a week later, for example, or by administering the mAb immediately prior to or after reperfusion. Preemptive use of mAb107 as used in this model can be of therapeutic benefit in a various clinical settings associated with development of AKI with no active treatments, for example, high-risk cardiac surgery (e.g. elective coronary artery bypass grafting), prior to chemotherapy or kidney transplantation. Ischemic AKI is a common complication of cardiac surgery especially in high-risk patients with renal hypoperfusion[64], and carries an increased risk of progression to CKD and long-term mortality[65,66]. Preoperative mAb107 administration may accelerate kidney recovery and prevent CKD in this setting. CD11b+ inflammatory cells play an important role in AKI-induced by Adriamycin: a mAb to CD11b/CD18 reduced renal injury in Adriamycin nephropathy by partially depleting CD11b+ macrophages[67]. Pretreatment with mAb107 is a safer and more effective alternative. FR AKI after kidney transplantation is also a major cause of delayed graft function[51], which negatively affects long-term graft survival[68]. Therapeutic strategies using mAb107 can be implemented in both donor and recipient, or by adding mAb107 to the perfusion fluid during machine preservation[69].

Therapeutic Compositions

In some embodiments, therapeutic compositions herein can interact with (e.g., bind, bind specifically and/or bind immunospecifically) binding partners (e.g., an immunogen(s), antigen(s), and/or epitope(s)) related to a disease or condition, wherein interaction between the therapeutic composition and the binding partners results in an improvement towards the condition or disease (e.g., a decrease in the level of disease or symptoms thereof in a subject).

In some embodiments, therapeutic compositions can include a polypeptide that immunospecifically binds the epitope recognized by mab107.

In some embodiments, the polypeptide can include (e.g., comprise, consist essentially of, or consist of) at least one (e.g., one, two, three, four, five, and/or six) complementarity determining region (CDR) of the variable heavy chain (VH) and/or variable light chain (VL) of antibody as shown in Table 1 (See also FIGS. 7 and 8). In some embodiments, therapeutic compositions can include polypeptides that include (e.g., comprise, consist essentially of, or consist of) at least one (e.g., one, two, or three) complementarity determining region (CDR) of the variable heavy chain (VH) and/or at least one (e.g., one, two, or three) complementarity determining region (CDR) variable light chain (VL) of antibody as shown in Table 1. In some embodiments, a polypeptide that immunospecifically binds the epitope recognized by mab107 is mab107 itself.

In some embodiments, therapeutic compositions can include polypeptides that include (e.g., comprise, consist essentially of, or consist of) at least one (e.g., one, two, three, four, five, and/or six) complementarity determining region (CDR) of the variable heavy chain (VH) and/or variable light chain (VL) of antibody as shown in Table 1, and that interact with (e.g., bind, bind specifically and/or bind immunospecifically) to integrin or integrin subunits (e.g. integrin alpha subunit CD11b), including epitopes thereof.

TABLE 1

Amino acid sequences of CDRs in mAb 107 VH and VL

|  | CDR1 | CDR2 | CDR3 |
| --- | --- | --- | --- |
| mAb 107 VH | GFNIKD | DPANDK | HYGYDGYA |
| mAb 107 VL | YSSNQKNY | WAS | YYSYPL |

In some embodiments, the affinity of binding between the polypeptide and integrin or integrin subunits (e.g. integrin alpha subunit CD11b) can be between about 0.1 nM to 1 µM, for example, about 10 nM.

In some embodiments, therapeutic compositions can include peptides (e.g., polypeptides), including for example, antibodies, including full length and/or intact antibodies, or antibody fragments. An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding portion") or single chain thereof, fusion proteins comprising an antibody, and any other modified configuration of the immunoglobulin molecule that comprises an antigen recognition site. An antibody includes an antibody of any class, such as IgG; IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG; and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively.

The subunit structures and three-dimensional configurations of different classes of immunoglobulins are well known. Exemplary antibodies and antibody fragments include, but are not limited to, monoclonal antibodies (including full-length monoclonal antibodies), polyclonal antibodies, multispecific antibodies formed from at least two different epitope binding fragments (e.g., bispecific antibodies), camelised antibodies, chimeric antibodies, single chain variable fragments (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above.

In some embodiments, antibodies or antibody fragments can be human or humanized. In some embodiments, the VH region in a humanized antibody or antibody fragment includes amino acid sequences as shown in FIG. 9. In some embodiments, the VL region in a humanized antibody or antibody fragment includes amino acid sequences as shown in FIG. 10.

Fragments of antibodies are suitable for use in the methods provided so long as they retain the desired affinity and specificity of the full-length antibody. Thus, a fragment of an antibody that binds the epitope recognized by mab107 will retain an ability to bind to the epitope recognized by mab107 in the Fv portion.

An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) can have the ability to recognize and bind antigen, although usually at a lower affinity than the entire binding site.

Single-chain Fv or (scFv) antibody fragments comprise the VH and VL domains of antibody, wherein these domains are present in a single polypeptide chain. Generally the Fv polypeptide further comprises a polypeptide linker between the VH and VL domains, which enables the scFv to form the desired structure for antigen binding. One exemplary scFV that immunospecifically binds the epitope recognized by mab107 is shown in FIG. 11. This scFV includes a humanized VH segment, a humanized VL segment, and a linker between these two segments.

The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

Diabodies are small antibody fragments with two antigen-binding sites, which fragments comprise a VH connected to a VL in the same polypeptide chain (VH and VL). By using a linker that is too short to allow pairing between the two domains on the same chain, the domains are forced to pair with the complementary domains of another chain and create two antigen-binding sites.

Linear antibodies comprise a pair of tandem Fd segments (VH-CH1-VH-CH1) which, together with complementary light chain polypeptides, form a pair of antigen binding regions. Linear antibodies can be bispecific or monospecific. Antibodies and antibody fragments of the present disclosure can be modified in the Fc region to provide desired effector functions or serum half-life.

In some embodiments, the Fc region can be conjugated to PEG or albumin to increase the serum half-life, or some other conjugation that results in the desired effect. Alternatively, where it is desirable to eliminate or reduce effector function, so as to minimize side effects or therapeutic complications, certain other Fc regions may be used.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs and in particular CDR3.

Therapeutic Composition Preparation

Polypeptides that immunospecifically bind the epitope recognized by mab107 can be prepared from hybridoma cells, for example, a hybridoma cell line deposited on Jan. 26, 2011, in the American Type Culture Collection (10801 University Blvd. Manassas, Va. 20110-2209) with Accession Number ATCC PTA-11614. mAb-containing supernatants harvested from hybridoma cultures are clarified and concentrated. The mAb can be purified on various chromatographs, for example, Protein A affinity chromatography, hydroxyapatite charge exchange chromatography and size-exclusion chromatography, etc. Endotoxin can removed by an endotoxin removing gel, such as Detoxi-Gel™ Endotoxin Removing Gel (Pierce, Rockford, Ill.). The level of endotoxin in the final product and in buffers can be determined with the Limulus Amebocyte Lysate (LAL) gel-clot test. mAb concentration can be determined by UV absorbance. Purity can be assessed by sodium dodecyl sulphate poly-acrylamide gel electrophoresis (SDS-PAGE) and Coomassie staining. The sterile and purified mAb can be stored at 4° C. until used. Detailed methods of preparing monoclonal antibodies are described, e.g., in U.S. Pat. No. 7,998,738B2; Horenstein, A. L., Durelli, I. & Malavasi, F. Purification of Clinical-Grade Monoclonal Antibodies by Chromatographic Methods. In Methods in Molecular Biology P. Therapeutic Proteins: Methods and Protocols (C Mark Smales and David C James., eds), Humana Press, Totowa, N.J., Chapter 16. (2005).

In some embodiments, polypeptides that immunospecifically bind the epitope recognized by mab107 can be prepared from immune cells and molecular biology techniques. Obtaining or targeting immune cells can include one or more and/or combinations of, for example: obtaining or providing a tetrameric immunogen (e.g., the epitope recognized by mab107) that can bind (e.g., bind specifically) to a target immune cell; contacting the tetrameric immunogen with a sample; detecting the tetrameric immunogen; determining whether the tetrameric immunogen is bound to a target immune cell; and, if the tetrameric immunogen is bound to a target immune cell, then obtaining the target immune cell.

Methods for isolating or purifying genetic material (e.g., DNA and/or mRNA) from the obtained target immune cell are known in the art and are exemplified herein. Once such genetic material has been obtained, methods for using it to produce the therapeutic compositions disclosed herein are known in the art and/or are summarized below. As discussed above, genetic material can be varied, using techniques known in the art to create polypeptide variants disclosed herein. Generating polypeptides from nucleic acids (e.g., cDNA) contained within or obtained from the target cell can include, for example, analysis, e.g., sequencing of heavy and light chain variable domains from target immune cells (e.g., single or isolated identified target immune cells).

In some embodiments, methods can include generating fully human antibodies, or fragments thereof (e.g., as disclosed above), and humanization of nonhuman antibodies. DNA can be readily isolated and/or sequenced from the obtained immune cells using conventional procedures (e.g., by using oligonucleotide probes that are capable of binding specifically to genes encoding the heavy and light chains of murine antibodies).

Once isolated, DNA can be placed into expression vectors, which are then transfected into host cells such as *Escherichia coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., :2 6-262 (1993) and Pluckthun, Immunol. Revs., 130:1 1-188 (1992).

Recombinant expression of an antibody or variant thereof generally requires construction of an expression vector containing a polynucleotide that encodes the antibody. The invention, thus, provides replicable vectors comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Once the expression vector is transferred to a host cell by conventional techniques, the transfected cells are then cultured by conventional techniques to produce an antibody. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In some embodiments, human cell lines developed by immortalizing human lymphocytes can be used to recombinantly produce monoclonal antibodies. In one embodiment, the human cell line PER.C6. (Crucell, Netherlands) can be used to recombinantly produce monoclonal antibodies.

In some embodiments, polypeptides disclosed herein can be generated synthetically. Synthetic chemistry transformations and protecting group methodologies (protection and deprotection) useful in synthesizing polypeptides described herein are known in the art and include, for example, those such as described in R. Larock, Comprehensive Organic Transformations, VCH Publishers (1989); T. W. Greene and P.G.M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Peptides can also be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH2 protected by either t-Boc or Fmoc chemistry using side chain protected amino acids on, for example, an Applied Biosystems Peptide Synthesizer Model 430A or 431.

Peptide bonds can be replaced, e.g., to increase physiological stability of the peptide, by: a retro-inverso bonds (C(O)—NH); a reduced amide bond (NH—CH2); a thiomethylene bond (S—CH2 or CH2-S); an oxomethylene bond (O—CH2 or CH2-O); an ethylene bond (CH2-CH2); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or CH3; and a fluoro-ketomethylene bond (C(O)—CFR or CFR—C(O) wherein R is H or F or CH3.

Peptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof. In some embodiments, peptides can be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences (referred to herein as "tags") described above or otherwise known in the art to facilitate purification. Peptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

In some embodiments, polypeptides can be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences (referred to herein as "tags") described above or otherwise known in the art to facilitate purification.

Therapeutic Use

The disclosure provides methods of treatment that include administering to a subject a composition disclosed herein.

The term "subject," as used herein, refers to any animal. In some embodiments, the subject is a mammal. In some embodiments, the term "subject", as used herein, refers to a human (e.g., a man, a woman, or a child). Samples for use in the methods can include serum samples, e.g., obtained from the selected subject.

In some embodiments, subject selection can include obtaining a sample from a subject (e.g., a candidate subject) and testing the sample for an indication that the subject is suitable for selection. In some embodiments, the subject can be confirmed or identified, e.g. by a health care professional, as having had or having a condition or disease. In some embodiments, exhibition of a positive response towards a condition or disease can be made from patient records, family history, and/or detecting an indication of a positive response. In some embodiments multiple parties can be included in subject selection. For example, a first party can obtain a sample from a candidate subject and a second party can test the sample. In some embodiments, subjects can be selected and/or referred by a medical practitioner (e.g., a general practitioner). In some embodiments, subject selection can include obtaining a sample from a selected subject and storing the sample and/or using the in the methods disclosed herein. Samples can include, for example, cells or populations of cells.

Ischemia Reperfusion Injuries

Mammal organs usually require a continuous supply of oxygen to maintain normal function. Under aerobic conditions, the organ tissue derives its energy primarily from the mitochondria. Following the onset of ischemia there is a rapid decline in high-energy phosphate levels with alterations in mitochondrial structure, volume, oxygen consumption, and ATP synthesis. Ischemia reperfusion injuries may affect various organs.

The methods described herein include methods for the treatment of disorders associated with ischemia reperfusion injuries in various organs, for example, kidney, heart, lung, brain etc. Many disorders are associated with ischemia reperfusion injuries. Methods described herein can be used to treat these disorders, for example, acute kidney injury, acute coronary syndrome, acute myocardial infarction, mesenteric ischemia, brain ischemia, stroke, acute limb ischemia, cyanosis, gangrene, etc.

The methods described herein also include methods of preventing or ameliorating a pathology caused by ischemia reperfusion injury, for example, chronic kidney disease, kidney fibroinflammatory diseases, post-ischemic renal fibrosis, post-MI left ventricular adverse remodeling, pulmonary fibrosis, ischemic colitis, etc.

Generally, the methods include administering a therapeutically effective amount of composition comprising a polypeptide that immunospecifically binds the epitope recognized by mab107, to a subject who is in need of, or who has been determined to be in need of, such treatment.

In some embodiments, a therapeutically effective amount of composition comprising a polypeptide that immunospecifically binds the epitope recognized by mab107 is administered to the subject within about 3 hours after the ischemia reperfusion injury, within about 2 hours after the ischemia reperfusion injury, within about 1.5 hours after the ischemia reperfusion injury, within about 1 hours after the ischemia reperfusion injury, within about 0.5 hours after the ischemia reperfusion injury.

Appropriate dosage and treatment regimen can be determined by an experienced clinician. In some embodiments, an therapeutically effective amount of composition comprising a polypeptide that immunospecifically binds the epitope recognized by mab107 can be administered to a subject. In some embodiments, an amount of 4-12 mg/Kg of the polypeptide (e.g., mab107) is administered to a subject.

In some embodiments, a polypeptide that immunospecifically binds the epitope recognized by mab107 is administered after the ischemia but before reperfusion occurs. In some embodiments, the polypeptide is administered after the reperfusion. In some embodiments, the intervention is preventive in nature. Thus, the polypeptide is administered to a subject who is likely to suffer ischemia reperfusion injury, but has not developed ischemia reperfusion injury. In some embodiments, the polypeptide is administered to the subject before the ischemia reperfusion injury.

Organ Transplantation

The ischemia-reperfusion injury is a very important problem during organ transplantation. Much damage in organ transplantation appears to be induced by reperfusion injury. Organs used for transplantation often undergoes lengthy periods of cold ischemic storage after devascularization and cold perfusion, resulting in an increased susceptibility to damage upon reperfusion. Ischemia/reperfusion injury often leads to delayed graft function.

Methods described herein include methods of reducing delayed graft function followed by organ transplantation, for example, heart transplantation, kidney transplantation, lung transplantation, live transplantation, bone marrow transplantation etc. In some embodiments, a polypeptide that immunospecifically binds the epitope recognized by mab107 can be used to control ischemia/reperfusion damage for transplanted organs. In some embodiments, a therapeutically effective amount of composition comprising a polypeptide that immunospecifically binds the epitope recognized by mab107 is administered to the organ recipient prior to, during, or after the organ transplantation procedure. In some embodiments, a therapeutically effective amount of composition comprising a polypeptide that immunospecifically binds the epitope recognized by mab107 is administered to the donor before the organ is harvested. In some embodiments, a therapeutically effective amount of composition comprising a polypeptide that immunospecifically binds the epitope recognized by mab107 administered to the transplanted organ, for example, the polypeptide can be injected into the blood vessels (e.g., arteries, veins) of the transplanted organ or directly injected into the organ tissue, or the polypeptide can be added to the perfusion fluid for organ preservation, when the retrieved organ is preserved in a preservation apparatus.

Autoimmune Disease

Autoimmune diseases arise from an abnormal immune response of the body against substances and tissues normally present in the body (autoimmunity). This may be restricted to certain organs (e.g. in autoimmune thyroiditis) or involve a particular tissue in different places (e.g. Goodpasture's disease which may affect the basement membrane in both the lung and the kidney).

Methods described herein includes methods of treating a subject having autoimmune diseases, for example, cytoplasmic antineutrophil cytoplasmic antibodies (cANCA)-associated vasculitis. In some embodiments, the methods include administering to the subject a therapeutically effective amount of composition comprising a polypeptide that immunospecifically binds the epitope recognized by mab107.

In some embodiments, a therapeutically effective amount of composition comprising a polypeptide that immunospecifically binds the epitope recognized by mab107 is administered to a subject with at least one or two other immunosuppression compositions, for example, glucocorticoid, cyclophosphamide, azathioprine, dactinomycin, methotrexate etc.

Diabetic Nephropathy

Diabetic nephropathy (or diabetic kidney disease) is a progressive kidney disease caused by damage to the capillaries in the kidneys' glomeruli. It is due to longstanding diabetes mellitus, and characterized by nephrotic syndrome and diffuse scarring of the glomeruli.

Methods described herein includes methods of treating a subject having diabetic nephropathy comprising. In some embodiments, the methods include administering to the subject a therapeutically effective amount of composition comprising a polypeptide that immunospecifically binds the epitope recognized by mab107.

Chemotherapy Toxicity

Chemotherapy is a common treatment for various cancers, however, it also causes several serious complications. Chemotherapy-induced organ toxicity is one complication that limits the clinical use of chemotherapeutic agents. For example, certain chemotherapeutic agents, such as anthracyclines, are highly effective against acute lymphoblastic and myeloblastic leukemias, but are particularly harmful to the heart due to its effects on mitochondria. Another example is Adriamycin. Adriamycin (doxorubicin) is an anthracycline, a class of anti-tumor drugs with a very wide spectrum of activity in human cancers. In humans, Adriamycin undergoes rapid plasma clearance and there is significant tissue binding. Adriamycin accumulates mainly in the kidney. This probably accounts for the greater nephrotoxicity, leading to Adriamycin nephropathy. These chemotherapies often induce organ failure by triggering inflammation. A monoclonal antibody that targets CD11b/CD18 can reduce renal injury in Adriamycin nephropathy by partially depleting CD11b+ macrophages (Wang, Y., et al. Partial depletion of macrophages by ED7 reduces renal injury in Adriamycin nephropathy. Nephrology (Carlton) 10, 470-477 (2005)). But in some cases, pretreatment with a polypeptide that immunospecifically binds the epitope recognized by mab107 may be a safer and more effective alternative, because the polypeptide that immunospecifically binds the epitope recognized by mab107 (e.g., mab107) does not deplete leukocytes.

Methods described herein includes methods of preventing or ameliorating a pathology caused by chemotherapy in a subject, for example, by reducing chemotherapy toxicity. One useful method to minimize chemotherapy-induced organ toxicity is to administer a therapeutically effective amount of composition comprising a polypeptide that immunospecifically binds the epitope recognized by mab107 to a subject that is currently under a chemotherapy treatment regimen. If the subject needs to be treated with chemotherapy (e.g., because prescribed by a physician or veterinarian), the subject can be treated with a polypeptide that immunospecifically binds the epitope recognized by mab107 before, during, and/or after administration of the chemotherapy. For example, subjects can be treated with a polypeptide that immunospecifically binds the epitope recognized by mab107 starting immediately after administering chemotherapy to a subject, as a singular treatment or continuing intermittently or continuously for about 1, 2, 5, 8, 10, 20, 30, 50, or 60 days, one year, indefinitely, or until a physician determines that administration of the polypeptide is no longer necessary.

Pharmaceutical Compositions

The methods described herein include the use of pharmaceutical compositions comprising a polypeptide that immunospecifically binds the epitope recognized by mab107 as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active composition in the required amount in an appropriate solvent with one or a combination of ingredients enumerated above, as required, followed by filtered sterilization. Generally, dispersions are prepared by incorporating the active composition into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active composition can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the composition can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic composition as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compositions are formulated into ointments, salves, gels, or creams as generally known in the art.

The pharmaceutical compositions can be included in a container, pack, or dispenser together with instructions for administration.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Example 1: Ligand-Mimetic mAb Antagonist of Leukocyte Integrin CD11b/CD18 Ameliorates Fibrosis and Kidney Failure Materials and Methods mAb Preparation mAb-containing supernatants harvested from hybridoma cultures were clarified and concentrated by circulating it through a hollow fiber membrane cartridge. The mAb was purified by successive steps on Protein A affinity chromatography, hydroxyapatite charge exchange chromatography and size-exclusion chromatography. Endotoxin was removed using Detoxi-Gel™ (Pierce, Rockford, Ill.) and its level in the final product and in buffers used in the purification was determined with the Limulus Amebocyte Lysate (LAL) gel-clot test. mAb concentration was determined by UV absorbance; purity assessed following sodium dodecyl sulphate polyacrylamide gel electrophoresis (SDS-PAGE) and Coomassie staining. The sterile and purified mAb was stored at 4° C. until used. Methods of preparing monoclonal antibodies are described, e.g., in Horenstein, A. L., Durelli, I. & Malavasi, F. Purification of Clinical-Grade Monoclonal Antibodies by Chromatographic Methods. In Methods in Molecular Biology P. Therapeutic Proteins: Methods and Protocols (C Mark Smales and David C James., eds), Humana Press, Totowa, N.J., Chapter 16. (2005).

Animal Procurement

Pathogen-free Cynomolgus (macaque) male monkeys were bought from Charles River Lab (Texas), weighed 2.6-4 kg and were approximately 2-3 years old. They were housed in wire-mesh cages in air-conditioned, humidity and temperature-controlled rooms with a 12-h light-dark cycle until use. Animals were fed LabDiet® 5038 and tap water ad libitum.

Animal Procedures

All procedures were approved by the Institutional Animal Care and Use Committee of Massachusetts General Hospital. Anti-coagulated blood was obtained from the saphenous vein. The monkeys were prepared for surgery. Briefly, animals were fasted overnight and then sedated with IM ketamine, 3.0-5.0 mg/kg plus Dexdomitor 0.03-0.06 mg/kg. Atropine, 0.05 mg/kg IM, was given. Anesthesia was achieved by administration of Isoflurane 1-3% inhalant with intermittent administration of ketamine as needed. The trachea was intubated and the animal ventilated with positive pressure and a gas mixture of 40% O2/60% N2, and BP continuously monitored. The chest, abdomen and posterior aspect of both calves were shaved. Intravenous normal saline solution containing 40 mg cefazoline was started in the saphenous vein using a #24 angiocatheter. Detailed methods of preparing monkeys for surgery and performing surgery on monkeys are described, e.g., in Haug, C. E., et al. Real-time monitoring of renal function during ischemic injury in the rhesus monkey. Ren Fail 17, 489-502 (1995).

Unilateral right kidney ischemia was induced by 2 hour hilar cross clamping. The contralateral ureter was ligated. Five animals were treated with mAb 107 (4-12 mg/Kg) and five with saline or the irrelevant mAb X63. One-half the mAb does was given prior to ischemia and the other half 2 minutes before reperfusion. The doses used were predicted to achieve blood levels of the mAb 7-12 fold greater than the half-maximal phagocytosis-inhibitory concentration ($K_i$~15 µg/ml) in vitro[71], and based on an estimated circulating blood volume of ~65 ml/kg of body weight for cynomolgus monkeys. 3-9 months post FR, the surgically exposed left ureter was religated 2 days prior to planned euthanasia and kidney function measured prior to and one and 2 days afterwards.

Open right kidney biopsies were carried out 1-2 days and one month after reperfusion. The right kidney was exposed following a midline abdominal incision, and a 2×4 mm incision extending approximately 1½ mm into the cortex made with the M75 blade. The wedge biopsy was then excised using iris scissors. Bleeding was controlled with finger pressure, and subcutaneous fat or muscle sutured into the cortical defect. After assuring hemostasis, the wound was closed in layers, the animal awakened, stable vital signs assured then returned to the housing area.

Animals were euthanized at the indicated times by intravenous administration of euthasol, 0.33 mg/kg (1 ml contains 390 mgs of pentobarbital and 50 mgs phenytoin). This method is consistent with the recommendation of the panel on Euthanasia of the American Veterinary Medical Association. Kidneys were exposed, inspected, the ureter and renal artery and vein were ligated and transected and the kidneys removed and submitted for testing.

Kidney sections for histology was placed in 4% formaldehyde, embedded in paraffin, and stained with hematoxylin/eosin or immunostained using antibodies. Sections for RNA analysis were placed immediately in 2-mL tubes containing RNAlater (Ambion), an RNA stabilization and protection agent. The tubes were refrigerated overnight at 4° C. and stored at −70° C. until ready for use.

Measurement of Non-Reflow

A videotape of the surgical procedure was used to measure the time taken for the ischemic dark purple-colored right kidney to change color back to red after right clamp release.

Quantitation of Peripheral Blood Leukocytes

Hematocrit, total white blood cells, neutrophils, monocytes, lymphocytes and platelets were quantified in heparinized blood using established methods.

Biochemical Determinations

Blood samples were allowed to clot and were centrifuged at high speed for 30 min. Serum was obtained and stored at −80° C. until use. BUN and sCR were measured in duplicates in 96-well plates using a colorimetric method. Mouse mAbs were measured using eBioscience mouse IgG total ELISA kit (Affymetrix, San Diego, Calif.) as described by the manufacturer.

Quantitation of cytokines, chemokines and complement C3 was performed in sera or extracts derived from equivalent amounts (by weight) of kidney tissue biopsy or autopsy using appropriate ELISA kits.

Leukocyte Isolation and Flow Cytometry

Monkey peripheral blood leukocytes were isolated from EDTA-anti-coagulated whole blood using Ammonium-Chloride-Potassium (ACK) erythrocyte lysis buffer (Lonza) as described by the manufacturer. The leukocyte pellet was washed twice with Dulbecco's Phosphate Buffered saline solution (DPBS, Gibco®). Leukocytes were incubated with or without 1 µl of mAb 107 (1 mg/ml) for 30 minutes in FACS-staining buffer (DPBS$^{++}$ solution+1% fetal calf serum) at room temperature, washed then incubated with 1 µl FITC-anti-mouse Fab (1.4 mg/ml, Jackson ImmunoResearch, West Grove, Pa.) for 20 minutes on ice. Cells were washed once with 0.5 ml FACS-staining buffer, fixed and analyzed using a FACSCalibur™ or LSRFortessa™ flow cytometer (BD Biosciences). mAb binding was expressed as mean fluorescence intensity, as determined using the FlowJo software (BD Biosciences). Monkey PMNs were isolated from EDTA-anti-coagulated blood by fractionation over lympholyte-poly solution (CEDARLANE, Burlington, ON) as described by the manufacturer. Washed cells were then stained with mAb107 as above.

Integrin Activation

Leukocytes ($1×10^6$ cells in 100 µl HBSS containing 1% globulin-free BSA (HBSS-BSA) and 1 mM each of $CaCl_2$ and $MgCl_2$) were treated with FMLF ($5×10^{-7}$ M final concentration) for 10 min at 37° C. Unlabeled Fab 107 was added to one half of the replicate tubes for an additional 30 min, followed by the addition of mouse mAb 24 to all of the tubes and incubation for an extra 20 min. Cells then were washed once, stained with the anti-Fc-specific fluorophore-labeled Ab (for 30 min at 0° C.), washed again, fixed with 1% formaldehyde in PBS, and analyzed by flow cytometry as above.

Immunocytochemistry

Air dried (30 min) frozen sections of normal human or monkey kidney for direct immunofluorescence are cut in a cryostat at a thickness of 2 to 4 mm. Afterward, slides are washed for 5 minutes in 0.01 M sodium-phosphate buffered saline (PBS)-0.15 M NaCl (pH 7.3) to remove unbound serum proteins. MPO$^+$ cells were identified. Detailed methods were described, e.g., in Farris, A. B., et al. Morphometric and visual evaluation of fibrosis in renal biopsies, *Journal of the American Society of Nephrology: JASN* 22, 176-186 (2011); Ysebaert, D. K., et al. Identification and kinetics of leukocytes after severe ischaemia/reperfusion renal injury, *Nephrol Dial Transplant* 15, 1562-1574 (2000).

Slides were incubated in monoclonal antibody for one hr. at room temperature at 1/30, 1/100, and 1/300 dilutions. After incubation, the slides are tipped to one side to allow the excess conjugate to run off and washed in PBS four times for 5 to 10 min each. Then, the slides were incubated with polyclonal anti-mouse (rabbit-FITC labeled) at 1/200 dilution (a known optimal dilution) for 1 hr. at room temperature. Slides were then again rinsed in PBS four times for 5-10 minutes each, and cover-slipped with mounting medium (Aqua-Mount, Lerner Labs, Pittsburgh, Pa.). The slides were then examined using a fluorescence microscope with epi-illumination equipment, which consists of barrier and excitation filters contained in a dichroic mirror package, to allow the visualization of fluorescein.

6 μm-thick serial sections were prepared and stained with hematoxylin/eosin or trichrome (Toulouse Latrec 1 Step Trichrome Stain Kit, Biocare Medical, Concord Park, Calif.). Fibrosis was expressed as the percent area that is Trichrome Stain-positive in ten fields at 20× magnification.

For collagen III immunohistochemistry (IHC), antigen retrieval was performed using the Borg Decloaker (Biocare Medical). Polyclonal rabbit anti-human collagen III (LS-B693; Lifespan Biosciences, Seattle, Wash.) was used at a dilution of 1:400. For collagen III morphometry, stained sections were scanned with an Aperio Scan-Scope CS (Aperio Technologies, Inc., Vista, Calif.) and analyzed using the ImageScope Positive Pixel Count algorithm (Aperio Technologies, Inc., Vista, Calif.). The Aperio Scanscope allowed scanning and quantitation of the whole slide using a 20× objective lens with a numerical aperture of 0.75 coupled with a doubler objective to achieve a scan of whole slides at 40× magnification. The default parameters of the Positive Pixel Count (hue of 0.1 and width of 0.5) detected collagen III IHC adequately. Collagen deposition was expressed as percent of pixels positive for anti-Col antibody.

Macrophages were identified with anti-CD68 mAb ED1 (Abcam, Cambridge, Mass.). Antibody binding was detected with Envision Dual Link System with horseradish peroxidase (Dako, Carpineria, Calif.) and developed with diaminobenzidine using the Autostainer Plus automated immunohistochemical stainer (Dako). Interstitial macrophage count was expressed as an average number in 20 fields at 200× magnification.

Quantitative Real-Time PCR

Total RNA was extracted from kidney tissue with an RNeasy kit and was treated with DNase according to the manufacturer's protocol (Qiagen, Hilden, Germany), and each sample was reverse-transcribed with MultiScribe reverse transcriptase (Applied Biosystems, Foster City, Calif.). Each 25-μl sample for quantitative PCR contained 2 μl of cDNA, 12.5 μl of 2×SYBR Green Master Mix (Applied Biosystems, Foster City, Calif.) and 250 nM of sense and antisense primers. Emitted fluorescence for each reaction was measured during the annealing/extension phase. The calculated number of copies was divided by the number of copies of the housekeeping gene glyceraldehyde-3-phosphate dehydrogenase (GAPDH).

Statistical Analysis

For comparisons data were analyzed by the two-tailed Student t-test. Values of p less than 5% were considered significant.

Results

A Nonhuman Primate Model of Post-Ischemic CKD

We modified an earlier model of ischemic AKI in non-human primates to assess the impact of severe AKI on chronic fibrosis and kidney failure (Haug, C. E., et al. Real-time monitoring of renal function during ischemic injury in the rhesus monkey. *Ren Fail* 17, 489-502 (1995)). In a pilot study of 2 Cynomolgus monkeys, we induced warm ischemic AKI by a two-hour right hilar cross clamping, with contralateral ligation of the left ureter. This lead to acute right kidney failure, necessitating release of left ureter ligature 2 days later to avoid animal death from uremia. Animals were then followed for several weeks, at which time the left ureter was again ligated and right kidney function measured one and 2 days later followed by animal sacrifice (FIG. 1). Non-life sustaining kidney failure developed on day 2 post left ureter ligation, and was associated with severe interstitial fibrosis in the harvested right kidney.

Effect of mAb107 on Right I/R AKI

Figures 2A, 2Q:
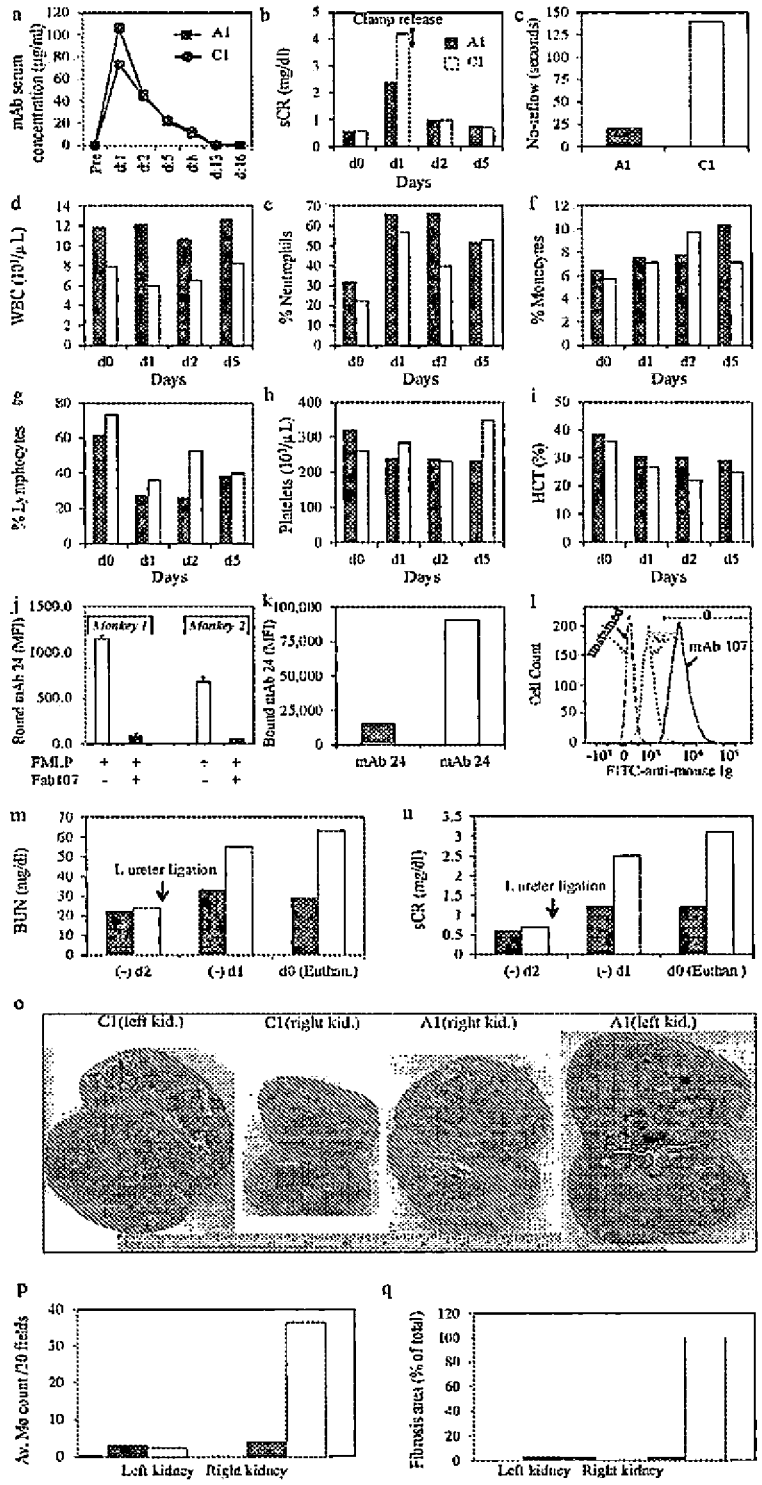
FIGS. 2a-2q. Effect of mAb107 on progression of acute kidney injury (AKI) to chronic kidney disease (CKD) in a treated and an untreated monkey.

The above CKD model was used to assess the role of CD11b$^+$ innate immune cells in acute and chronic kidney injury in a pair of healthy Cynomolgus monkeys. One animal (A1, 4.2 kg) received intravenous mAb107 at 6 mg/kg, with ½ the dose given 2 minutes prior to ischemia and the other half 2 minutes before reperfusion. The control animal (C1, 3.0 kg) received an equal dose of an IgG1-matched nonreactive mouse mAb X63 (ATCC). The surgical team was blinded as to which animal received the respective mAb. Serum creatinine (Cr) and blood urea nitrogen (BUN) were measured prior to and during left ureter ligation to assess right kidney function. Right kidney biopsies were performed one day after ischemia, at which time the serum levels of mAbs 107 and X63 were 105.6 μg/ml and 73.8 μg/ml, respectively. These levels were similar on day 2 and became undetectable by day 13 (FIG. 2a). Right kidney biopsy was repeated one month after AKI. Three months after right AKI and two days before planned euthanasia, the left ureter was again ligated for 2 days, and Cr levels measured daily. Both kidneys were harvested after animal sacrifice.

Serum Cr rose by four- and seven fold in A1 and C1, respectively, one day after I/R (FIG. 2b). Release of the contralateral left ureteral ligature normalized serum Cr in both animals two and five days after right AKI (FIG. 2b). Upon release of the right vascular obstruction, the no-reflow time, a reflection of the microvasculature perfusion rate, was 32 sec in A1 vs. 84 sec in C1. Portions of C1 right kidney retained the mottled appearance (FIG. 2c). mAb107 did not result in depletion of peripheral white blood cells, neutrophils, monocytes, lymphocytes, platelets, or red blood cells on days 1, 2 and 5 post injury (FIG. 2d-i). A blinded histopathologic examination of right kidney biopsy one day after injury did not find an appreciable difference in the extent of acute tubular necrosis between the two animals, but found decreased interstitial MPO+ leukocytes in the cortical-medullary area in the treated vs. control kidney.

mAb107 Inhibited Integrin Activation mAb107 is known to prevent agonist-induced conformational switching of human cellular CD11b/CD18 from its native inactive state to the active proadhesive state[35]. Binding of mAb107 to polymorphonuclear cells (PMNs) isolated from two naïve monkeys also blocked activation of monkey CD11b/CD18 induced by the chemoattractant f-met-leu-phe (FMLF), as reported by binding of the activation-sensitive mAb 24[38] (FIG. 2j). mAb107 also reduced integrin activation on monkey PMNs in vivo: flow cytometric analysis showed higher binding of APC-mAb24 to control PMNs obtained one day after AKI when compared with binding to PMNs from the treated monkey (FIG. 2k). That the latter cells already had bound mAb107 on their surface was demonstrated by the selective binding of FITC-labeled goat anti-mouse Ig (FIG. 2l).

Recovery of Right Kidney Function in the mAb-07-Treated Animal 3 Months after I/R Blinded histopathologic examination of right kidney biopsy obtained one month after AKI showed 5% interstitial fibrosis in the treated animal vs. 15% in control, suggesting that mAb107 promotes kidney recovery. Because of the potential bias in biopsy tissue sampling, right kidney function was measured 3 months after AKI by religation of the contralateral left ureter for two days, with daily measurements of urea nitrogen (BUN) and serum Cr. BUN/Cr rapidly rose in the control from normal pre-ligation levels (22 mg/dL/0.7 mg/dL) to 55/2.5 and 63/3.1 one and two days after left ureter ligation, respectively (FIGS. 2m-n). In contrast, BUN/Cr from a baseline of 22/0.6 in the treated animal to 33/1.2 and 29/1.2 one and two days, respectively, after left ureter ligation (FIGS. 2m-n).

The two animals were then euthanized on day 2 post left ureter ligation, and the left and right kidneys harvested, visually examined and submitted for histopathologic studies. The control right kidney was adherent to the surrounding tissue, and much smaller than the control left kidney, with thinning of the outer cortex (FIG. 2o). In contrast, the treated right kidney that did not adhere to the surrounding tissue, and was only slightly smaller than the left kidney (FIG. 2o). Histopathologic examination of the left kidney showed acute tubular injury secondary to obstruction and largely resolved acute tubular necrosis in the right kidney. Intrarenal macrophages, interstitial fibrosis (FIGS. 2p-q) and collagen deposition were all reduced in the right kidney of the treated vs. control animal.

Right Kidney Evaluation in Four Additional Pairs of Monkeys 1-2 Days after I/R

Figures 3A, 3B, 3C, 3D, 3E, 3F, 3G, 3H, 3I, 3J:
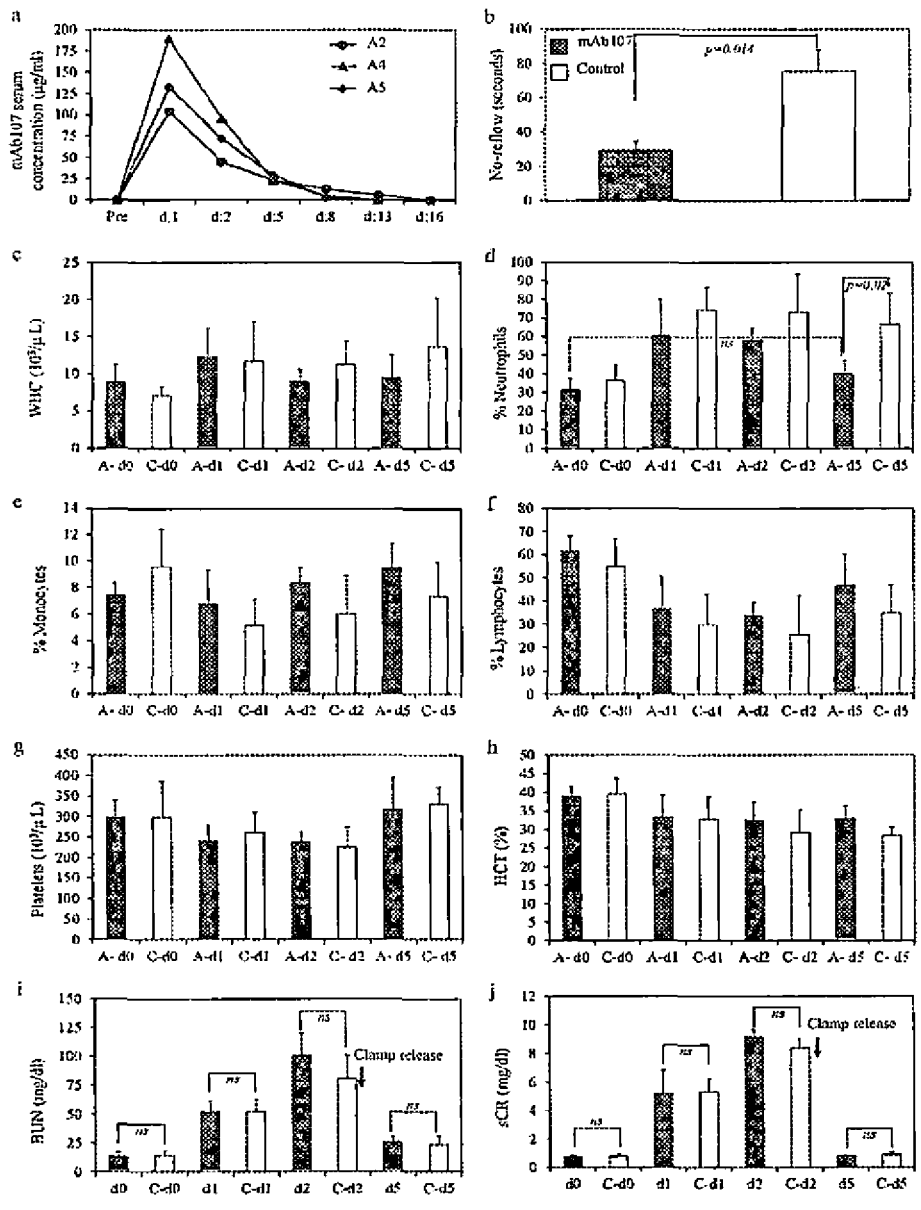
FIGS. 3a-3j. Effect of mAb107 on AKI.

To assess the significance of the above findings in a larger cohort, and the longer-term effects on kidney function, the above studies were repeated in eight additional monkeys, four in each of the treated and control groups. We also extended the follow up period to 6 months after I/R in two pairs (A2/C2, A3/C3) and to 9 month in the two others (A4/C4, A5/C5). Serum levels of mAb107 measured in three of the four treated animals yielded values comparable to those seen in A1 above, and followed a similar half-life (FIG. 3a).

No-reflow was again shortened in the four treated animals vs. controls (FIG. 3b). mAb107 did not reduce circulating red blood cells, leukocytes or platelets 1, 2 and 5 days after I/R (FIG. 3c-h), with neutrophil counts returning to baseline on day five vs. those in controls (FIG. 3d), perhaps reflecting persistent inflammation in the control animals. BUN and Cr also rose to equivalent degrees in the two groups one and two days after left ureter ligation, and returned to normal by day five after release of left ureter ligature (FIGS. 3i-j).

Right kidney biopsies performed on day 2 after AKI showed comparable degrees of acute tubular necrosis in the treated and control groups (FIGS. 3k-l).

Assessment of Kidney Function and Histopathology 6-9 Months after AKI

Figures 4A, 4B, 4C, 4D, 4E, 4F, 4G, 4H, 4I:
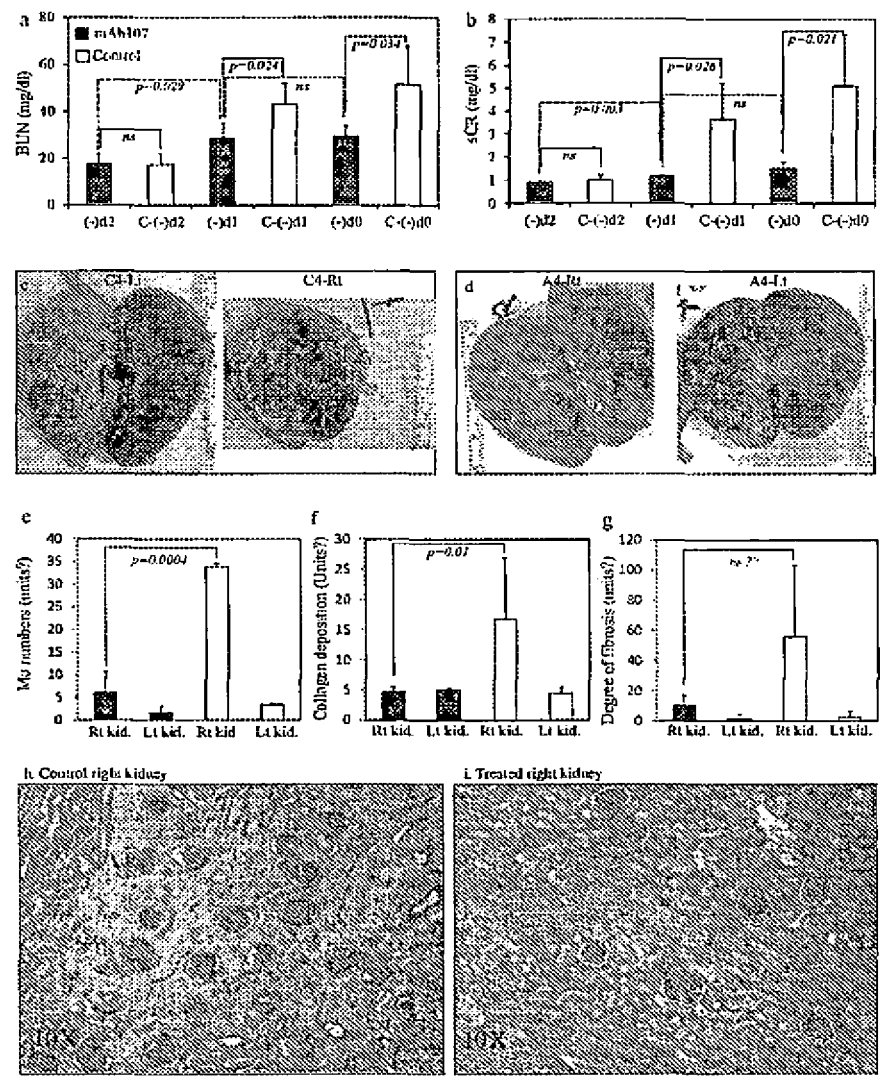
FIGS. 4a-4i. mAb107 salvaged right kidney function several months after AKI.

Right kidney function was measured 6 and 9 months after AKI and one and two days following re-ligation of the contralateral left ureter in seven of the eight animals (3 treated and four controls). BUN and Cr were significantly lower in the mAb-107-treated group one day after religation (BUN=28.5±6.61 mg/dL, Cr=1.15±0.08 mg/dL) vs. controls (BUN=43.2±8.73 mg/dL, Cr=3.64±1.59 mg/dL), did not rise further the following day vs. controls (BUN=51.2±6.0 mg/dL, Cr=5.08±2.24 mg/dL) (FIGS. 4a-b). The BUN/Cr in treated animals approached but remained significantly higher than the baseline levels prior to left ureter ligation (BUN=17.25±4.43 mg/dL, Cr=0.87±0.06 mg/dL) (FIGS. 4a-b).

Harvested control right kidneys were more adherent to surrounding tissue, were visibly smaller and of abnormal architecture when compared with their left counterparts or with right kidneys from mAb107-treated animals (representative shown in FIGS. 4c-d). Histopathologic examination of kidneys from each of the mAb107-treated animals showed tubular recovery, with absent or only focal areas of fibrosis (FIGS. 4h-i). Quantitative assessments showed significant reductions in interstitial leukocytes and collagen deposition vs. controls (FIGS. 4e-h).

Cytokine/Chemokine Profiles 24 Hours after Reperfusion

Chemokines, cytokines and complement have been suggested to play an important pathogenic role in rodent models of I/R AKI[10]. To assess the impact of inactivation of CD11b/CD18 on early changes in these inflammatory mediators, we quantified serum and tissue levels of thirteen such mediators in two treated and two control animals, one to two days after AKI, as well in the harvested left and right kidneys at sacrifice. Tissue protein levels of right kidney biopsies obtained 1-2 days post I/R showed marked reductions in RANTES, IL18, complement C3, IFN-γ and IL6 vs. control kidneys. mRNA levels for Variable changes were found in levels of TNFα, IL8, MCP1, IL1Rα and active TGFβ, but levels of IL2 and IL1β were increased in the treated kidneys (FIG. 5a).

Figures 5A, 5B:
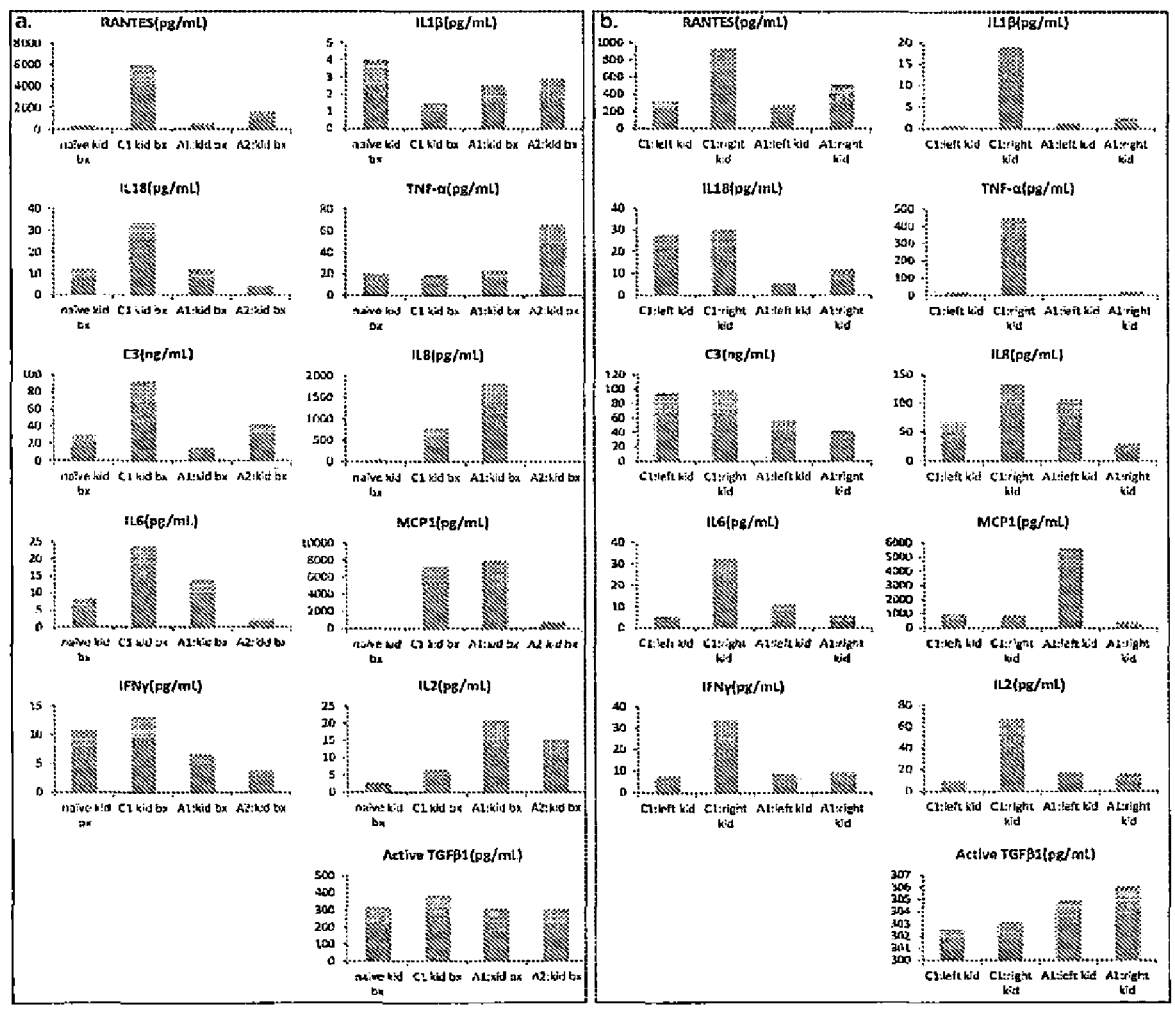
FIGS. 5a-5b. Effect of mAb107 on kidney levels of inflammatory mediators.

In right kidneys harvested 3 and 6 months after AKI from treated animals, protein levels of all measured mediators except for active TGFβ were much reduced vs. control right kidney (FIG. 5b). Interestingly, levels of IL8, MCP1, IL1Rα were elevated in the left treated kidney. mRNA levels of RANTES, IL18, IL6 and HIF1α but not IL17a were reduced in right kidneys of treated animals vs. control (FIG. 5b).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

LIST OF REFERENCES

1. Solez, K., Morel-Maroger, L. & Sraer, J. D. The morphology of "acute tubular necrosis" in man: analysis of 57

1. renal biopsies and a comparison with the glycerol model. *Medicine (Baltimore)* 58, 362-376 (1979).
2. Rabb, H., et al. Inflammation in AKI: Current Understanding, Key Questions, and Knowledge Gaps. *Journal of the American Society of Nephrology: JASN* (2015).
3. Lameire, N. H., et al. Acute kidney injury: an increasing global concern. *Lancet* 382, 170-179 (2013).
4. Susantitaphong, P., et al. World incidence of AKI: a meta-analysis. *Clinical journal of the American Society of Nephrology: CJASN* 8, 1482-1493 (2013).
5. Chertow, G. M., Burdick, E., Honour, M., Bonventre, J. V. & Bates, D. W. Acute kidney injury, mortality, length of stay, and costs in hospitalized patients. *Journal of the American Society of Nephrology: JASN* 16, 3365-3370 (2005).
6. Boros, P. & Bromberg, J. S. New cellular and molecular immune pathways in ischemia/reperfusion injury. *Am J Transplant* 6, 652-658 (2006).
7. Lo, L. J., et al. Dialysis-requiring acute renal failure increases the risk of progressive chronic kidney disease. *Kidney international* 76, 893-899 (2009).
8. Nelson, P. J., et al. The renal mononuclear phagocytic system. *Journal of the American Society of Nephrology: JASN* 23, 194-203 (2012).
9. Lupher, M. L., Jr. & Gallatin, W. M. Regulation of fibrosis by the immune system. *Adv Immunol* 89, 245-288 (2006).
10. Eltzschig, H. K. & Eckle, T. Ischemia and reperfusion—from mechanism to translation. *Nature medicine* 17, 1391-1401 (2011).
11. Kurts, C., Panzer, U., Anders, H. J. & Rees, A. J. The immune system and kidney disease: basic concepts and clinical implications. *Nat Rev Immunol* 13, 738-753 (2013).
12. Li, L., et al. NKT cell activation mediates neutrophil IFN-gamma production and renal ischemia-reperfusion injury. *J Immunol* 178, 5899-5911 (2007).
13. Li, L., et al. The chemokine receptors CCR2 and CX3CR1 mediate monocyte/macrophage trafficking in kidney ischemia-reperfusion injury. *Kidney international* 74, 1526-1537 (2008).
14. Gandolfo, M. T., et al. Foxp3+ regulatory T cells participate in repair of ischemic acute kidney injury. *Kidney international* 76, 717-729 (2009).
15. Wynn, T. A. & Ramalingam, T. R. Mechanisms of fibrosis: therapeutic translation for fibrotic disease. *Nature medicine* 18, 1028-1040 (2012).
16. Clements, M., et al. Differential Ly6C Expression after Renal Ischemia-Reperfusion Identifies Unique Macrophage Populations. *Journal of the American Society of Nephrology: JASN* 27, 159-170 (2016).
17. Murray, P. J., et al. Macrophage activation and polarization: nomenclature and experimental guidelines. *Immunity* 41, 14-20 (2014).
18. Cerda, J., et al. *Promoting Kidney Function Recovery in Patients with AKI* Requiring RRT. *Clinical journal of the American Society of Nephrology: CJASN* 10, 1859-1867 (2015).
19. Molitoris, B. A., Okusa, M. D., Palevsky, P. M., Kimmel, P. L. & Star, R. A. Designing clinical trials in acute kidney injury. *Clinical journal of the American Society of Nephrology: CJASN* 7, 842-843 (2012).
20. Mestas, J. & Hughes, C. C. Of mice and not men: differences between mouse and human immunology. *J Immunol* 172, 2731-2738 (2004).
21. Lim, B. J., Yang, H. C. & Fogo, A. B. Animal models of regression/progression of kidney disease. *Drug Discov Today Dis Models* 11, 45-51 (2014).
22. Arnaout, M. A. Structure and function of the leukocyte adhesion molecules CD11/CD18. *Blood* 75, 1037-1050 (1990).
23. Wagner, C., et al. The complement receptor 3, CR3 (CD11b/CD18), on T lymphocytes: activation-dependent up-regulation and regulatory function. *Eur J Immunol* 31, 1173-1180 (2001).
24. Lahmers, K. K., et al. Comparative gene expression by WC1+ gammadelta and CD4+ alphabeta T lymphocytes, which respond to *Anaplasma marginale*, demonstrates higher expression of chemokines and other myeloid cell-associated genes by WC1+ gammadelta T cells. *J Leukoc Biol* 80, 939-952 (2006).
25. Pilling, D., Fan, T., Huang, D., Kaul, B. & Gomer, R. H. Identification of markers that distinguish monocyte-derived fibrocytes from monocytes, macrophages, and fibroblasts. *PLoS One* 4, e7475 (2009).
26. Arnaout, M. A., et al. Deficiency of a granulocyte-membrane glycoprotein (gp150) in a boy with recurrent bacterial infections. *N Engl J Med* 306, 693-699 (1982).
27. Evangelista, V., et al. Platelet/polymorphonuclear leukocyte interaction in dynamic conditions: evidence of adhesion cascade and cross talk between P-selectin and the beta 2 integrin CD11b/CD18. *Blood* 88, 4183-4194 (1996).
28. Parkos, C. A., Delp, C., Arnaout, M. A. & Madara, J. L. Neutrophil migration across a cultured intestinal epithelium. Dependence on a CD11b/CD18-mediated event and enhanced efficiency in physiological direction. *The Journal of clinical investigation* 88, 1605-1612 (1991).
29. Annenkov, A., Ortlepp, S. & Hogg, N. The beta 2 integrin Mac-1 but not p150,95 associates with Fc gamma RIIA. *Eur J Immunol* 26, 207-212 (1996).
30. Zhou, M. J. & Brown, E. J. CR3 (Mac-1, alpha M beta 2, CD11b/CD18) and Fc gamma RIII cooperate in generation of a neutrophil respiratory burst: requirement for Fc gamma RIII and tyrosine phosphorylation. *The Journal of cell biology* 125, 1407-1416 (1994).
31. van Spriel, A. B., et al. Mac-1 (CD11b/CD18) is essential for Fc receptor-mediated neutrophil cytotoxicity and immunologic synapse formation. *Blood* 97, 2478-2486 (2001).
32. Ingalls, R. R., Arnaout, M. A. & Golenbock, D. T. Outside-in signaling by lipopolysaccharide through a tailless integrin. *J Immunol* 159, 433-438 (1997).
33. Wu, H., et al. TLR4 activation mediates kidney ischemia/reperfusion injury. *The Journal of clinical investigation* 117, 2847-2859 (2007).
34. Castano, A. P., et al. Serum amyloid P inhibits fibrosis through Fc gamma R-dependent monocyte-macrophage regulation in vivo. *Sci Transl Med* 1, 5ra13 (2009).
35. Mahalingam, B., et al. Stable coordination of the inhibitory Ca2+ ion at the metal ion-dependent adhesion site in integrin CD11b/CD18 by an antibody-derived ligand aspartate: implications for integrin regulation and structure-based drug design. *J Immunol* 187, 6393-6401 (2011).
36. Cox, D., Brennan, M. & Moran, N. Integrins as therapeutic targets: lessons and opportunities. *Nat Rev Drug Discov* 9, 804-820 (2010).
37. Haug, C. E., et al. Real-time monitoring of renal function during ischemic injury in the rhesus monkey. *Ren Fail* 17, 489-502 (1995).
38. Kamata, T., et al. The role of the CPNKEKEC sequence in the beta(2) subunit I domain in regulation of integrin alpha(L)beta(2) (LFA-1). *J Immunol* 168, 2296-2301 (2002).

39. Hsu, C. Y. Yes, AKI truly leads to CKD. *Journal of the American Society of Nephrology: JASN* 23, 967-969 (2012).
40. Rifkin, D. E., Coca, S. G. & Kalantar-Zadeh, K. Does AKI truly lead to CKD? *Journal of the American Society of Nephrology: JASN* 23, 979-984 (2012).
41. Devarajan, P. Update on mechanisms of ischemic acute kidney injury. *Journal of the American Society of Nephrology: JASN* 17, 1503-1520 (2006).
42. Flores, J., DiBona, D. R., Beck, C. H. & Leaf, A. The role of cell swelling in ischemic renal damage and the protective effect of hypertonic solute. *The Journal of clinical investigation* 51, 118-126 (1972).
43. Summers, W. K. & Jamison, R. L. The no reflow phenomenon in renal ischemia. *Lab Invest* 25, 635-643 (1971).
44. Siedlecki, A., Irish, W. & Brennan, D. C. Delayed graft function in the kidney transplant. *Am J Transplant* 11, 2279-2296 (2011).
45. Kielar, M. L., et al. Maladaptive role of IL-6 in ischemic acute renal failure. *Journal of the American Society of Nephrology: JASN* 16, 3315-3325 (2005).
46. Yu, T. M., et al. RANTES mediates kidney ischemia reperfusion injury through a possible role of HIF-1alpha and LncRNA PRINS. *Sci Rep* 6, 18424 (2016).
47. Wu, H., et al. IL-18 contributes to renal damage after ischemia-reperfusion. *Journal of the American Society of Nephrology: JASN* 19, 2331-2341 (2008).
48. Thurman, J. M., Ljubanovic, D., Edelstein, C. L., Gilkeson, G. S. & Holers, V. M.
Lack of a functional alternative complement pathway ameliorates ischemic acute renal failure in mice. *J Immunol* 170, 1517-1523 (2003).
49. Ling, G. S., et al. Integrin CD11b positively regulates TLR4-induced signalling pathways in dendritic cells but not in macrophages. *Nat Commun* 5, 3039 (2014).
50. Burne, M. J., et al. IL-1 and TNF independent pathways mediate ICAM-1/VCAM-1 up-regulation in ischemia reperfusion injury. *J Leukoc Biol* 70, 192-198 (2001).
51. Cugini, D., et al. Inhibition of the chemokine receptor CXCR2 prevents kidney graft function deterioration due to ischemia/reperfusion. *Kidney international* 67, 1753-1761 (2005).
52. Furuichi, K., et al. CCR2 signaling contributes to ischemia-reperfusion injury in kidney. *Journal of the American Society of Nephrology: JASN* 14, 2503-2515 (2003).
53. Granucci, F., et al. Inducible IL-2 production by dendritic cells revealed by global gene expression analysis. *Nat Immunol* 2, 882-888 (2001).
54. Nelson, B. H. IL-2, regulatory T cells, and tolerance. *J Immunol* 172, 3983-3988 (2004).
55. Kinsey, G. R., et al. Regulatory T cells suppress innate immunity in kidney ischemia-reperfusion injury. *Journal of the American Society of Nephrology: JASN* 20, 1744-1753 (2009).
56. Bach, J. F. Regulatory T cells under scrutiny. *Nat Rev Immunol* 3, 189-198 (2003).
57. Aster, R. H., Curtis, B. R., McFarland, J. G. & Bougie, D. W. Drug-induced immune thrombocytopenia: pathogenesis, diagnosis, and management. *J Thromb Haemost* 7, 911-918 (2009).
58. Rabb, H., et al. Role of CD11a and CD11b in ischemic acute renal failure in rats. *Am J Physiol* 267, F1052-1058 (1994).
59. Booster, M., et al. Inhibition of CD18-dependent leukocyte adherence by mAb 6.5 E does not prevent ischemia-reperfusion injury as seen in grafted kidneys. *Transpl Int* 8, 126-132 (1995).
60. Tajra, L. C., et al. In vivo effects of monoclonal antibodies against rat beta(2) integrins on kidney ischemia-reperfusion injury. *J Surg Res* 87, 32-38 (1999).
61. Thornton, M. A., Winn, R., Alpers, C. E. & Zager, R. A. An evaluation of the neutrophil as a mediator of in vivo renal ischemic-reperfusion injury. *The American journal of pathology* 135, 509-515 (1989).
62. Rezzonico, R., Imbert, V., Chicheportiche, R. & Dayer, J. M. Ligation of CD11b and CD11c beta(2) integrins by antibodies or soluble CD23 induces macrophage inflammatory protein 1alpha (MIP-1alpha) and MIP-1beta production in primary human monocytes through a pathway dependent on nuclear factor-kappaB. *Blood* 97, 2932-2940 (2001).
63. Jakus, Z., Berton, G., Ligeti, E., Lowell, C. A. & Mocsai, A. Responses of neutrophils to anti-integrin antibodies depends on costimulation through low affinity Fc gamma Rs: full activation requires both integrin and nonintegrin signals. *J Immunol* 173, 2068-2077 (2004).
64. Thiele, R. H., Isbell, J. M. & Rosner, M. H. AKI associated with cardiac surgery. *Clinical journal of the American Society of Nephrology: CJASN* 10, 500-514 (2015).
65. Ishani, A., et al. The magnitude of acute serum creatinine increase after cardiac surgery and the risk of chronic kidney disease, progression of kidney disease, and death. *Arch Intern Med* 171, 226-233 (2011).
66. Hobson, C. E., et al. Acute kidney injury is associated with increased long-term mortality after cardiothoracic surgery. *Circulation* 119, 2444-2453 (2009).
67. Wang, Y., et al. Partial depletion of macrophages by ED7 reduces renal injury in Adriamycin nephropathy. *Nephrology (Carlton)* 10, 470-477 (2005).
68. Yarlagadda, S. G., Coca, S. G., Formica, R. N., Jr., Poggio, E. D. & Parikh, C. R. Association between delayed graft function and allograft and patient survival: a systematic review and meta-analysis. *Nephrol Dial Transplant* 24, 1039-1047 (2009).
69. Moers, C., et al. Machine perfusion or cold storage in deceased-donor kidney transplantation. *N Engl J Med* 360, 7-19 (2009).
70. Horenstein, A. L., Durelli, I. & Malavasi, F. Purification of Clinical-Grade Monoclonal Antibodies by Chromatographic Methods. In Methods in Molecular Biology P. Therapeutic Proteins: Methods and Protocols (C Mark Smales and David C James., eds), Humana Press, Totowa, N.J., Chapter 16. (2005).
71. Li, R., et al. Characterization of a conformationally sensitive murine monoclonal antibody directed to the metal ion-dependent adhesion site face of integrin CD11b. *J Immunol* 168, 1219-1225 (2002).
72. Farris, A. B., et al. Morphometric and visual evaluation of fibrosis in renal biopsies. *Journal of the American Society of Nephrology: JASN* 22, 176-186 (2011).
73. Ysebaert, D. K., et al. Identification and kinetics of leukocytes after severe ischaemia/reperfusion renal injury. *Nephrol Dial Transplant* 15, 1562-1574 (2000).

What is claimed is:

1. A method of ameliorating post-ischemic renal fibrosis in a subject comprising:
    administering to the subject a composition comprising a therapeutically effective amount of an antibody that immunospecifically binds CD11b, wherein the antibody comprises the following complementarity determining regions (CDRs):
    1) CDR 1 of the VH of mab107;
    2) CDR 1 of the VL of mab107;
    3) CDR 2 of the VH of mab107;
    4) CDR 2 of the VL of mab107;
    5) CDR3 of the VH of mab107; and
    6) CDR 3 of the VL of mab107.

2. The method of claim 1, wherein the composition is administered to the subject within about 5 hours after the ischemia reperfusion injury.

3. The method of claim 1, wherein is administered to the subject within about 2 hours after the ischemia reperfusion injury.

4. The method of claim 1, wherein the antibody comprises an amino acid sequence from the group consisting of:

(SEQ ID NO: 1)
QVQLQQSGAELVKPGASVKLSCTPSGFNIKDIYMQWVKQRPEQGLEW

IGRIDPANDKTKYDPKFQGKATITADTSSNTAYLQLSSLTSEDTAVY

YCASEGHYGYDGYAMDYWGQGTTVTVSS;

(SEQ ID NO: 2)
DIEMTQSPSSLGVSVGEKVTMSCKSSQNLLYSSNQKNYLAWYQQKPG

QSPKLLIYWASTRESGVPDRFTGTGSGTDFTLTISSVKAEDLAVYYC

QQYYSYPLTFGAGTKLELK;

(SEQ ID NO: 3)
VQLVESGGGLVQPGGSLRLSCAASGFNIKDTYIHWVRQAPGKGLEWV

ARIDPANDKTRYADSVKGRFTISADTSKNTAYLQMNSLRAEDTAVYY

CSSEGHYGYDGYAMDYWGQGTLVTVSS;

(SEQ ID NO: 4)
DIVMSQSPDSLAVSLGERVTLNCKSSQNLLYSSNQKNYLAWYQQKPG

QSPKLLIYWASARESGVPDRFSGSGSGTDFTLTISSVQAEDVAVYYC

QQYYSYPLTFGAGTKLELK;
and (SEQ ID NO: 5)
MVQLVESGGGLVQPGGSLRLSCAASGFNIKDTYIHWVRQAPGKGLEW

VARIDPANDKTRYADSVKGRFTISADTSKNTAYLQMNSLRAEDTAVY

YCSSEGHYGYDGYAMDYWGQGTLVTVSSGGGGSGGGGSGGGGSDIVM

SQSPDSLAVSLGERVTLNCKSSQNLLYSSNQKNYLAWYQQKPGQSPK

LLIYWASARESGVPDRFSGSGSGTDFTLTISSVQAEDVAVYYCQQYY

SYPLTFGAGTKLELK.

* * * * *

UNITED STATES PATENT AND TRADEMARK OFFICE
CERTIFICATE OF CORRECTION

PATENT NO. : 10,738,121 B2  
APPLICATION NO. : 15/553925  
DATED : August 11, 2020  
INVENTOR(S) : M. Amin Arnaout Page 1 of 1

It is certified that error appears in the above-identified patent and that said Letters Patent is hereby corrected as shown below:

On the Title Page

Column 2 (Other Publications), Line 5, delete "anti-CDIIb" and insert -- anti-CD11b --

Column 2 (Other Publications), Line 9, delete "Anti-CDIIb" and insert -- Anti-CD11b --

Column 2 (Other Publications), Line 16, after "al." insert --   --

In the Claims

In Column 39, Line 50 (approx.), Claim 4, after "sequence" insert -- selected --

Signed and Sealed this  
Twenty-fourth Day of January, 2023

Katherine Kelly Vidal  
*Director of the United States Patent and Trademark Office*

SEQUENCE LISTING

<160> NUMBER OF SEQ ID NOS: 12

<210> SEQ ID NO 1
<211> LENGTH: 122
<212> TYPE: PRT
<213> ORGANISM: Mus musculus

<400> SEQUENCE: 1

Gln Val Gln Leu Gln Gln Ser Gly Ala Glu Leu Val Lys Pro Gly Ala
1               5                   10                  15

Ser Val Lys Leu Ser Cys Thr Pro Ser Gly Phe Asn Ile Lys Asp Ile
            20                  25                  30

Tyr Met Gln Trp Val Lys Gln Arg Pro Glu Gln Gly Leu Glu Trp Ile
        35                  40                  45

Gly Arg Ile Asp Pro Ala Asn Asp Lys Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Glu Gly His Tyr Gly Tyr Asp Gly Tyr Ala Met Asp Tyr Trp
            100                 105                 110

Gly Gln Gly Thr Thr Val Thr Val Ser Ser
        115                 120

<210> SEQ ID NO 2
<211> LENGTH: 113
<212> TYPE: PRT
<213> ORGANISM: Mus musculus

<400> SEQUENCE: 2

Asp Ile Glu Met Thr Gln Ser Pro Ser Ser Leu Gly Val Ser Val Gly
1               5                   10                  15

Glu Lys Val Thr Met Ser Cys Lys Ser Ser Gln Asn Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Thr Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 3
<211> LENGTH: 121
<212> TYPE: PRT
<213> ORGANISM: Artificial Sequence
<220> FEATURE:
<223> OTHER INFORMATION: Humanized mAb107 VH domain

<400> SEQUENCE: 3

Val Gln Leu Val Glu Ser Gly Gly Gly Leu Val Gln Pro Gly Gly Ser
1               5                   10                  15

Leu Arg Leu Ser Cys Ala Ala Ser Gly Phe Asn Ile Lys Asp Thr Tyr

```
            20                  25                  30
Ile His Trp Val Arg Gln Ala Pro Gly Lys Gly Leu Glu Trp Val Ala
         35                  40                  45

Arg Ile Asp Pro Ala Asn Asp Lys Thr Arg Tyr Ala Asp Ser Val Lys
 50                  55                  60

Gly Arg Phe Thr Ile Ser Ala Asp Thr Ser Lys Asn Thr Ala Tyr Leu
65                   70                  75                  80

Gln Met Asn Ser Leu Arg Ala Glu Asp Thr Ala Val Tyr Tyr Cys Ser
                 85                  90                  95

Ser Glu Gly His Tyr Gly Tyr Asp Gly Tyr Ala Met Asp Tyr Trp Gly
            100                 105                 110

Gln Gly Thr Leu Val Thr Val Ser Ser
            115                 120
```

<210> SEQ ID NO 4
<211> LENGTH: 113
<212> TYPE: PRT
<213> ORGANISM: Artificial Sequence
<220> FEATURE:
<223> OTHER INFORMATION: Humanized mAb107 VL domain

<400> SEQUENCE: 4

```
Asp Ile Val Met Ser Gln Ser Pro Asp Ser Leu Ala Val Ser Leu Gly
1               5                   10                  15

Glu Arg Val Thr Leu Asn Cys Lys Ser Ser Gln Asn Leu Leu Tyr Ser
             20                  25                  30

Ser Asn Gln Lys Asn Tyr Leu Ala Trp Tyr Gln Gln Lys Pro Gly Gln
         35                  40                  45

Ser Pro Lys Leu Leu Ile Tyr Trp Ala Ser Ala Arg Glu Ser Gly Val
 50                  55                  60

Pro Asp Arg Phe Ser Gly Ser Gly Ser Gly Thr Asp Phe Thr Leu Thr
65                   70                  75                  80

Ile Ser Ser Val Gln Ala Glu Asp Val Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys
```

<210> SEQ ID NO 5
<211> LENGTH: 250
<212> TYPE: PRT
<213> ORGANISM: Artificial Sequence
<220> FEATURE:
<223> OTHER INFORMATION: humanized single chain variable fragment of 107
      (scVF) with a linker linking VH and VL segments

<400> SEQUENCE: 5

```
Met Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Asp Pro Ala Asn Asp Lys Thr Arg Tyr Ala Asp Ser Val
 50                  55                  60

Lys Gly Arg Phe Thr Ile Ser Ala Asp Thr Ser Lys Asn Thr Ala Tyr
65                   70                  75                  80
```

```
Leu Gln Met Asn Ser Leu Arg Ala Glu Asp Thr Ala Val Tyr Tyr Cys
                85                  90                  95

Ser Ser Glu Gly His Tyr Gly Tyr Asp Gly Tyr Ala Met Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Asp Ile Val Met Ser Gln Ser
        130                 135                 140

Pro Asp Ser Leu Ala Val Ser Leu Gly Glu Arg Val Thr Leu Asn Cys
145                 150                 155                 160

Lys Ser Ser Gln Asn Leu Leu Tyr Ser Ser Asn Gln Lys Asn Tyr Leu
                165                 170                 175

Ala Trp Tyr Gln Gln Lys Pro Gly Gln Ser Pro Lys Leu Leu Ile Tyr
            180                 185                 190

Trp Ala Ser Ala Arg Glu Ser Gly Val Pro Asp Arg Phe Ser Gly Ser
            195                 200                 205

Gly Ser Gly Thr Asp Phe Thr Leu Thr Ile Ser Ser Val Gln Ala Glu
        210                 215                 220

Asp Val Ala Val Tyr Tyr Cys Gln Gln Tyr Tyr Ser Tyr Pro Leu Thr
225                 230                 235                 240

Phe Gly Ala Gly Thr Lys Leu Glu Leu Lys
                245                 250

<210> SEQ ID NO 6
<211> LENGTH: 6
<212> TYPE: PRT
<213> ORGANISM: Mus musculus

<400> SEQUENCE: 6

Gly Phe Asn Ile Lys Asp
1               5

<210> SEQ ID NO 7
<211> LENGTH: 6
<212> TYPE: PRT
<213> ORGANISM: Mus musculus

<400> SEQUENCE: 7

Asp Pro Ala Asn Asp Lys
1               5

<210> SEQ ID NO 8
<211> LENGTH: 8
<212> TYPE: PRT
<213> ORGANISM: Mus musculus

<400> SEQUENCE: 8

His Tyr Gly Tyr Asp Gly Tyr Ala
1               5

<210> SEQ ID NO 9
<211> LENGTH: 8
<212> TYPE: PRT
<213> ORGANISM: Mus musculus

<400> SEQUENCE: 9

Tyr Ser Ser Asn Gln Lys Asn Tyr
1               5

<210> SEQ ID NO 10
```

```
<211> LENGTH: 6
<212> TYPE: PRT
<213> ORGANISM: Mus musculus

<400> SEQUENCE: 10

Tyr Tyr Ser Tyr Pro Leu
1               5

<210> SEQ ID NO 11
<211> LENGTH: 224
<212> TYPE: PRT
<213> ORGANISM: Mus musculus

<400> SEQUENCE: 11

Gln Val Gln Leu Gln Gln Ser Gly Ala Glu Leu Val Lys Pro Gly Ala
1               5                   10                  15

Ser Val Lys Leu Ser Cys Thr Pro Ser Gly Phe Asn Ile Lys Asp Ile
            20                  25                  30

Tyr Met Gln Trp Val Lys Gln Arg Pro Glu Gln Gly Leu Glu Trp Ile
        35                  40                  45

Gly Arg Ile Asp Pro Ala Asn Asp Lys Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Glu Gly His Tyr Gly Tyr Asp Gly Tyr Ala Met Asp Tyr Trp
            100                 105                 110

Gly Gln Gly Thr Thr Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Pro Arg Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

<210> SEQ ID NO 12
<211> LENGTH: 220
<212> TYPE: PRT
<213> ORGANISM: Mus musculus

<400> SEQUENCE: 12

Asp Ile Glu Met Thr Gln Ser Pro Ser Ser Leu Gly Val Ser Val Gly
1               5                   10                  15

Glu Lys Val Thr Met Ser Cys Lys Ser Ser Gln Asn Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60
```

```
Pro Asp Arg Phe Thr Gly Thr Gly Ser Gly Thr Asp Phe Thr Leu Thr
 65              70              75              80

Ile Ser Ser Val Lys Ala Glu Asp Leu Ala Val Tyr Tyr Cys Gln Gln
                 85              90              95

Tyr Tyr Ser Tyr Pro Leu Thr Phe Gly Ala Gly Thr Lys Leu Glu Leu
             100             105             110

Lys Arg Ala Asp Ala Ala Pro Thr Val Ser Ile Phe Pro Pro Ser Ser
         115             120             125

Glu Gln Leu Thr Ser Gly Gly Ala Ser Val Val Cys Phe Leu Asn Asn
     130             135             140

Phe Tyr Pro Lys Asp Ile Asn Val Lys Trp Lys Ile Asp Gly Ser Glu
145             150             155             160

Arg Gln Asn Gly Val Leu Asn Ser Trp Thr Asp Gln Asp Ser Lys Asp
             165             170             175

Ser Thr Tyr Ser Met Ser Ser Thr Leu Thr Leu Thr Lys Asp Glu Tyr
             180             185             190

Glu Arg His Asn Ser Tyr Thr Cys Glu Ala Thr His Lys Thr Ser Thr
         195             200             205

Ser Pro Ile Val Lys Ser Phe Asn Arg Asn Glu Cys
    210             215             220
```